(12) United States Patent
More

(10) Patent No.: US 10,830,754 B2
(45) Date of Patent: Nov. 10, 2020

(54) AUTOMATED PROFILING OF THE CONDITION OF WOOD

(71) Applicant: Osmose Utilities Services, Inc., Peachtree City, GA (US)

(72) Inventor: Randal K. More, Lafayette, NY (US)

(73) Assignee: Osmose Utilities Services, Inc., Peachtree City, GA (US)

( * ) Notice: Subject to any disclaimer, the term of this patent is extended or adjusted under 35 U.S.C. 154(b) by 0 days.

(21) Appl. No.: 16/135,484

(22) Filed: Sep. 19, 2018

(65) Prior Publication Data

US 2020/0088711 A1   Mar. 19, 2020

(51) Int. Cl.
| | |
|---|---|
| *H04N 7/18* | (2006.01) |
| *G01N 33/46* | (2006.01) |
| *G01N 21/95* | (2006.01) |
| *H04N 5/225* | (2006.01) |
| *G06T 7/00* | (2017.01) |

(52) U.S. Cl.
CPC ............ *G01N 33/46* (2013.01); *G01N 21/95* (2013.01); *G06T 7/0004* (2013.01); *H04N 5/2252* (2013.01); *H04N 5/2253* (2013.01); *H04N 5/2256* (2013.01); *H04N 5/2258* (2013.01); *H04N 2005/2255* (2013.01)

(58) Field of Classification Search
CPC combination set(s) only.
See application file for complete search history.

(56) References Cited

U.S. PATENT DOCUMENTS

| | | | |
|---|---|---|---|
| 2,835,127 A | 5/1958 | Scott | |
| 2,865,198 A | 12/1958 | Tschirf et al. | |
| 3,805,599 A | 4/1974 | Illman et al. | |
| 4,182,163 A | 1/1980 | Hoffmeyer | |
| 4,249,414 A | 2/1981 | Barth | |
| 4,343,179 A | 8/1982 | Astrom et al. | |
| 6,029,522 A * | 2/2000 | Schafer | G01N 29/2493 73/587 |
| 6,134,954 A | 10/2000 | Suresh et al. | |
| 6,289,734 B1 | 9/2001 | Daugela | |
| 9,869,622 B2 | 1/2018 | More et al. | |
| 2005/0005699 A1 | 1/2005 | Huang | |
| 2007/0046289 A1 | 3/2007 | Troxler | |
| 2013/0194413 A1* | 8/2013 | Hatcher | G02B 23/2476 348/82 |
| 2015/0233806 A1* | 8/2015 | More | G01N 3/42 73/85 |
| 2016/0287063 A1* | 10/2016 | Ramanujam | A61B 1/0676 |

FOREIGN PATENT DOCUMENTS

| | | |
|---|---|---|
| FR | 2760842 A1 | 9/1998 |
| SE | 504564 C2 | 3/1997 |
| SE | 519874 C2 * | 5/1997 |
| SE | 519874 C2 | 4/2003 |

OTHER PUBLICATIONS

Search Report from related U.K. Patent Application No. 1913064.0 dated Feb. 10, 2020.

* cited by examiner

*Primary Examiner* — Peet Dhillon
(74) *Attorney, Agent, or Firm* — Troutman Pepper Hamilton Sanders LLP

(57) ABSTRACT

A device for evaluating the condition of a wooden structure, including: a shaft; a distance sensor coupled to the shaft; and an image capture device coupled to the shaft, the distance sensor being configured to measure a location of the image capture device in the wooden structure.

17 Claims, 21 Drawing Sheets

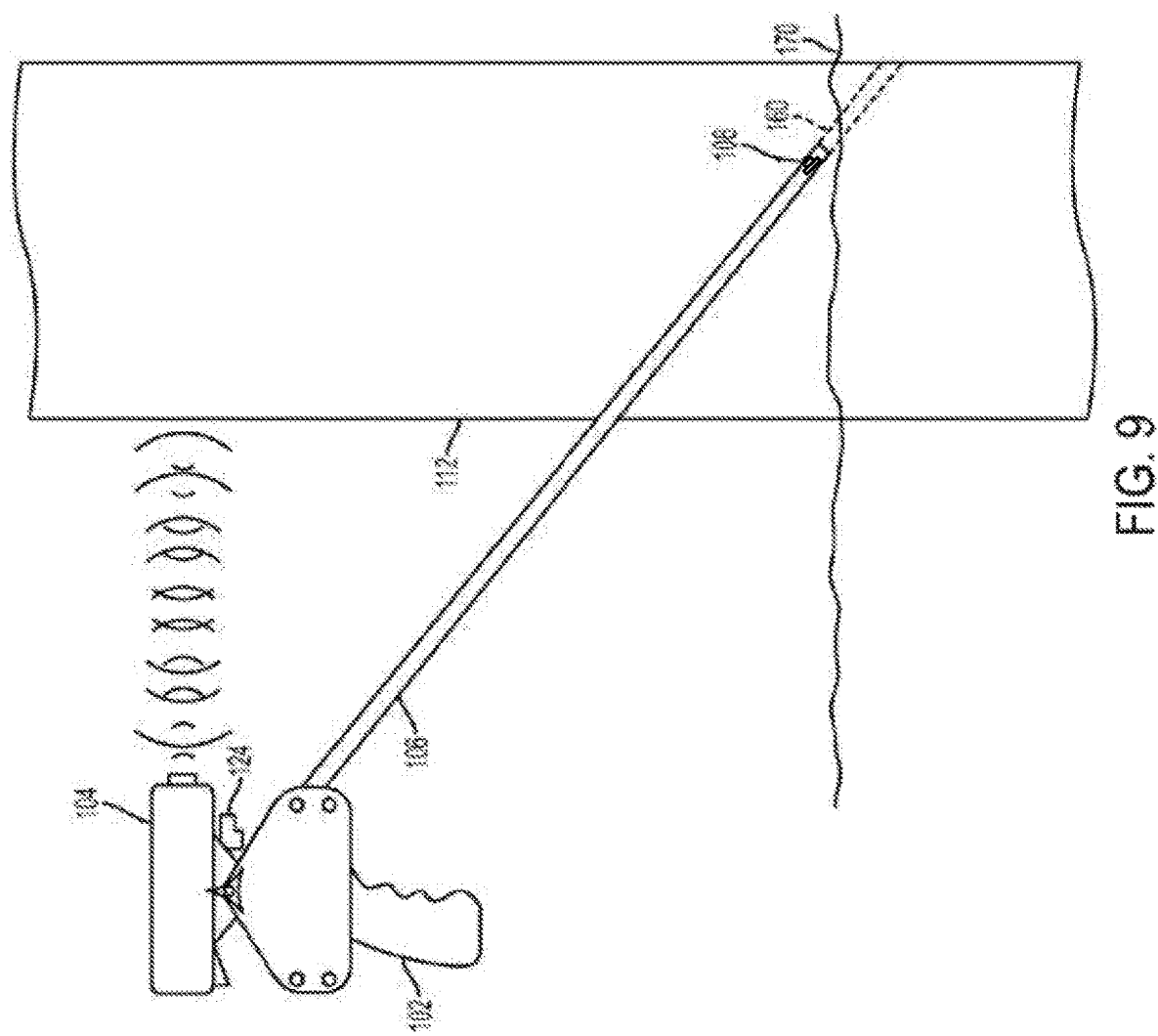

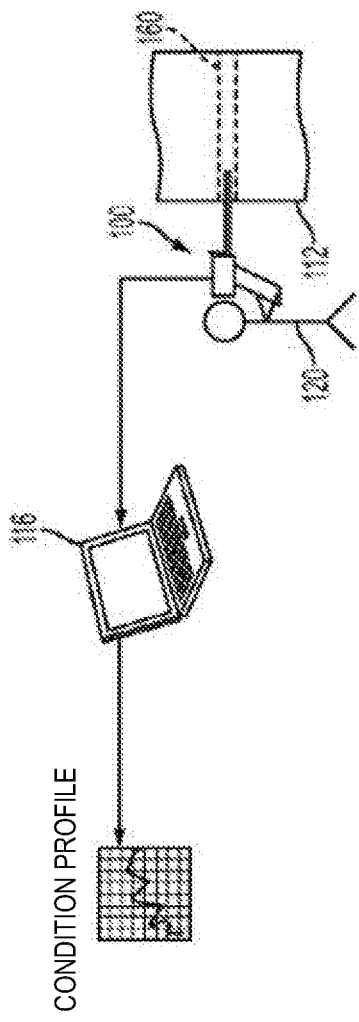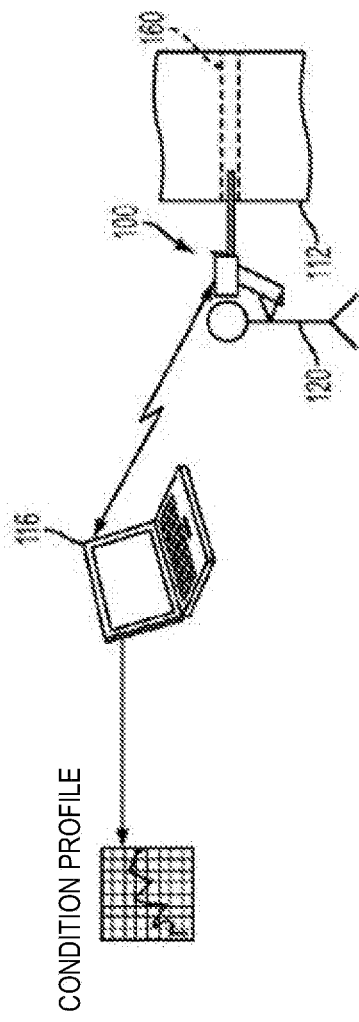

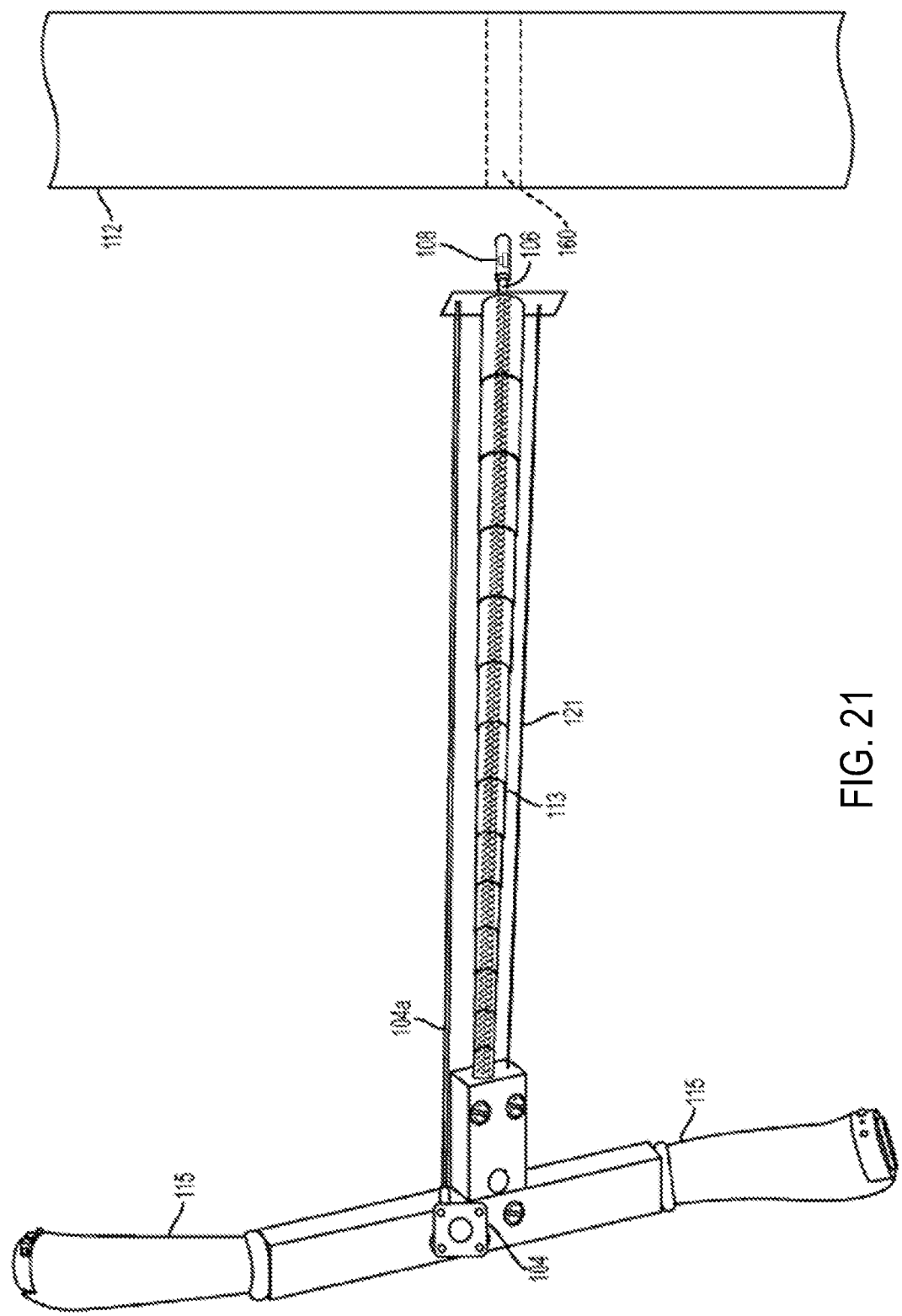

AUTOMATED PROFILING OF THE CONDITION OF WOOD

TECHNICAL FIELD

The disclosed technology pertains to a device, system, and method for evaluating the condition of a wooden structure by automated profiling of the condition of the structure. More particularly, embodiments of the disclosed technology are directed toward a probing device comprising an image capture device, for observing the condition of wood in a structure; a system comprising such a device, and a computing device coupled to the device that outputs a condition profile of the device; and a method for operating such a device and determining the condition of wood by identifying changes in conditions in a wooden structure.

BACKGROUND

The regular inspection of wooden structures such as utility poles, support pilings, and other timber structures is an essential part of the maintenance and upkeep of such structures. Aging wood can suffer from internal decay and/or rot as a result of insect and fungal infestations, as well as the presence of excessive moisture in the wood, and can develop voids, cracks, and cavities in its structure. Such flaws in the structural integrity of a utility pole or other wooden structure can lead to a loss of strength in the structure, decreasing the load that may be borne by the structure and in some cases necessitating restoration or even replacement. Therefore, accurate and repeatable methods of assessing the condition of wooden structures are required to minimize the risks associated with the aging of these structures.

The keys to utility pole inspection are identifying decay, measuring defects and estimating the percent remaining strength to determine whether the utility pole passes or fails the inspection, or requires remedial attention, such as supplemental wood preservative treatment, or reinforcement or restoration. Attempts to develop pole inspection instruments have not yet fully succeeded to add value or lower costs, and there is a need in the art for alternatives to the methods and devices that currently exist for the evaluation of utility poles.

Wood is a highly variable material and there are many possible decay patterns that are possible in any particular utility pole. These decay patterns also differ by the species of wood. The most accurate option for pole inspection remains a highly trained, professional inspector using time-proven procedures and tools. Some of these procedures include the following:

Visual inspection, or visual inspection combined with sound inspection procedures are typically suitable for identifying gross defects in utility poles that may be visible above the ground level. Using the visual inspection technique, trained personnel inspect the exterior of a utility pole or other wooden structure looking for structural deficiencies such as visible cracks, fissures, and splits in the surface of the structure, plant life or algae growing on the wood, holes bored by woodpeckers, and insects. Visual inspection, alone, may be suitable for identifying gross defects visible in a wooden structure, but can produce variable results that depend on the experience and the diligence of the particular inspector.

Sound and bore procedures allow an inspector to bore inspection holes after hammer sounding identifies areas where decay may exist in a utility pole. A shell thickness indicator may also be used to measure internal decay. For example, "sound and prod" and "sound and bore" techniques involve inspection personnel "sounding" the structure by striking it with a hammer, spike, or other instrument and listening to the resulting sound for hollow-sounding noises or other audible indications of internal deficiencies. The inspection personnel next may engage in "prodding" or "probing" the pole by inserting a screwdriver, drill, or other boring tool to sample the interior of the pole or other structure in a search for decay or damage. Personnel may also scrape the exterior of the wood to look for surface decay.

Partial excavation plus sound and bore procedures allow an inspector to access a portion of the pole below ground. These procedures are useful for the identification of external decay and termites or other insects. Excavation to a depth of 18 inches to 24 inches plus sound and bore techniques allow the most complete access to the decay-prone region of poles, where moisture and oxygen encourage decay.

Electronic inspection devices are instruments that typically depend on theories, such as frequency or time of flight of a sonic wave, or physical characteristics such as condition of wood to identify anomalies in a utility pole. For example, the Shigometer can identify early stages of decay, but it is not a pass/fail device. Other non-invasive or minimally-invasive inspection methods use equipment such as the Resistograph®, which measures the energy required to maintain a constant drilling speed in a wooden structure, or the Pilodyn penetrometer, which measures the depth into which a pre-loaded spring forces a pin into the surface of a wooden structure.

There remains a need in the art for alternative minimally-invasive techniques to complement existing techniques for the inspection of utility poles and other wooden structures, particularly for the detection of incipient decay and external decay below ground without excavation. The devices, systems, and methods of the disclosed technology are designed to meet this and other needs.

SUMMARY

The above needs and others may be addressed by some implementations of the disclosed technology.

In some embodiments, the distance sensor of the probing device may be mounted to a shaft, and an image capture device may be mounted to the shaft. In some embodiments, the distance sensor may be capable of measuring a location of the image capture device in the wooden structure.

In some embodiments, the image capture device, and the distance sensor are components of a single device. In some embodiments, a camera cover permits the image capture device to be covered when the probe may be inserted into the wooden structure, where the camera cover retracts and exposes the image capture device when the probe is removed, so that the image capture device can collect data as the probe is moved out of the wooden structure.

The disclosed technology may be directed, in some embodiments, to a system for evaluating the condition of a wooden structure comprising: a probing device, the probing device including a shaft, a distance sensor, and an image capture device; and a machine for receiving and processing data from the probing device, wherein the machine may be linked to the probing device. In some embodiments, the machine receives from the probing device visual data from the image capture device of the interior surfaces of the wooden structure, and the location of the image capture device when the visual data was captured.

The disclosed technology may be directed, in some embodiments, to methods for evaluating the condition of a wooden structure, comprising inserting an image capture device into the structure, the image capture device being coupled to an electronics unit; determining a location of the image capture device within the wooden structure with a distance sensor; capturing visual data of the interior surfaces of the wooden structure using the image capture device; and moving the image capture device deeper in the wooden structure while continuing to determine the location of the image capture device within the structure and continuing to capture visual data using the image capture device.

In some embodiments, the appearance of the interior surfaces of the wooden structure, as captured in visual data collected by the image capture device, indicates the condition of the wood surrounding the image capture device at a location within the structure. In some embodiments, the condition of the structure indicates the condition of the wood at a location within the structure.

In some embodiments, the methods further comprise recording a plurality of visual data collected by the image capture device at a plurality of locations within the structure, each amount corresponding to one location, to create a condition profile of the structure; and, in some embodiments, further comprising comparing a condition profile of the structure to a reference condition profile to determine the condition of the structure.

By way of example, when a wooden structure may be first placed into service, the condition of the wood therein may be expected to be essentially homogenous. As used herein, "condition" refers to the state of a structure relative to "reference wood." The term "reference wood" refers to wood that may be substantially undegraded. Different states of a structure relative to reference wood include but are not limited to intact, dried wood, such as the type of wood present in a wooden structure when the structure may be first placed into service, wood with elevated moisture content, which may be one indication of pre-decay, decayed wood, damaged wood (including but not limited to mechanical damage), and the like.

Changes in the condition of wood within a wooden structure are indicative of a change in the condition of the wood within the structure. When the condition of the wood surrounding the image capture device may essentially be the same as the condition of the reference wood, the condition of the evaluated wood may be considered "normal." As used herein, "normal" or "normal wood" refers to wood that displays essentially the same condition profile as a reference wood. "Normal wood" has the same condition as "reference wood." When the condition of the wood surrounding the image capture device may be different (not essentially the same) than "reference wood," the condition of the evaluated wood may be considered "decayed," "damaged" or "altered."

BRIEF DESCRIPTION OF THE FIGURES

Appended FIGS. 1-21 depict some non-limiting embodiments of the probing device, the system for evaluating wooden structures comprising the probing device, and the methods of evaluating and maintaining wooden structures using the probing device and/or system. The figures are not intended to limit the scope of the disclosed technology, but, instead, are intended to provide depictions of specific embodiments, features, and non-limiting characteristics of the devices, systems, and methods described herein.

FIG. 1 depicts a side view of an example device according to an example embodiment of the disclosed technology.

FIG. 2 depicts an end of an example device according to an example embodiment of the disclosed technology, wherein the shaft comprises a probing tip that surrounds the image capture device.

FIG. 3 depicts an end of an example device according to an example embodiment of the disclosed technology, wherein a distance sensor and a handle are attached to the shaft.

FIG. 4 depicts an example device according to an example embodiment of the disclosed technology, with the shaft removed from the distance sensor and handle.

FIG. 5 depicts the manner in which a removable shaft may be connected to the handle and distance sensor according to an example embodiment.

FIG. 6 depicts the probing tip removed from the shaft according to an example embodiment.

FIG. 7 depicts a side view of an example device according to an example embodiment of the disclosed technology.

FIG. 8 depicts an angled view of an example device according to an example embodiment of the disclosed technology.

FIG. 9 depicts a short-range sonar at a non-zero angle to the shaft of an example device according to an example embodiment of the disclosed technology.

FIGS. 11A and 11B depict an example system according to an example embodiment of the disclosed technology for evaluating the condition of a wooden structure.

FIG. 12 depicts a "profile" from an evaluation of the hardness of the wooden structure in a utility pole according to an example embodiment.

FIG. 13 depicts a flow chart outlining steps of one or more example methods to assess and maintain a utility pole according to certain embodiments of the disclosed technology.

FIG. 14 depicts an end of an example device according to an example embodiment of the disclosed technology, wherein the shaft comprises a tube, a probing tip that surrounds the image capture device, and pins securing the device together.

FIG. 15 depicts an internal assembly of the end of the example device shown in FIG. 14, wherein the tube portion of the shaft is removed.

FIG. 16 depicts an end of an example device according to an example embodiment of the disclosed technology, wherein a distance sensor, a handle, and a dial are attached to the shaft.

FIG. 17 depicts an electronics unit of an example device according to an example embodiment of the disclosed technology.

FIG. 18 depicts a side view of an example device according to an example embodiment of the disclosed technology, wherein the distance sensor is a string potentiometer, and the shaft is angled downward.

FIG. 19 depicts an overhead view of an example device according to an example embodiment of the disclosed technology.

FIG. 20 depicts an overhead view of a distance sensor, using collapsible scissors and potentiometer, according to an example embodiment of the disclosed technology.

FIG. 21 depicts a side view of a distance sensor, using a compression sleeve and string potentiometer, according to an example embodiment of the disclosed technology.

DETAILED DESCRIPTION

Figure 1:
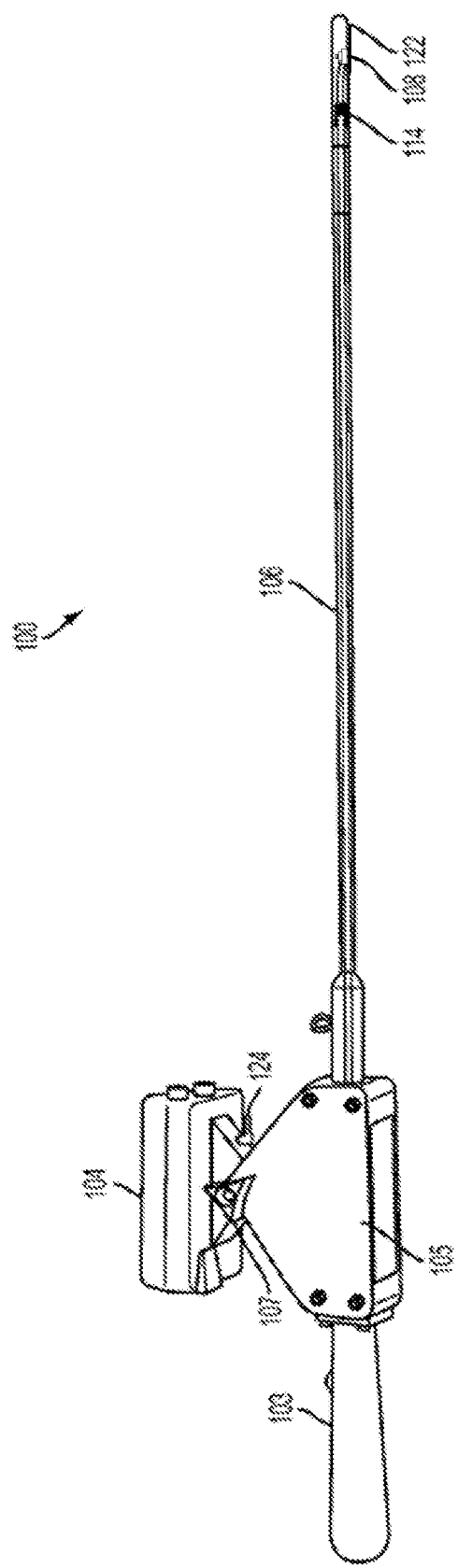

The present disclosure may be understood more readily by reference to the following detailed description of example embodiments and the examples included herein. Before the example embodiments of the devices and methods according to the present disclosure are disclosed and described, it is to be understood that embodiments are not limited to those described within this disclosure. Numerous modifications and variations therein will be apparent to those skilled in the art and remain within the scope of the disclosure. It is also to be understood that the terminology used herein is for the purpose of describing specific embodiments only and is not intended to be limiting. Some embodiments of the disclosed technology will be described more fully hereinafter with reference to the accompanying drawings. This disclosed technology may, however, be embodied in many different forms and should not be construed as limited to the embodiments set forth therein.

In the following description, numerous specific details are set forth. However, it is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "some embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Unless otherwise noted, the terms used herein are to be understood according to conventional usage by those of ordinary skill in the relevant art. In addition to any definitions of terms provided below, it is to be understood that as used in the specification and in the claims, "a" or "an" can mean one or more, depending upon the context in which it is used. Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Also, in describing the example embodiments, terminology will be resorted to for the sake of clarity. It is intended that each term contemplates its broadest meaning as understood by those skilled in the art and includes all technical equivalents that operate in a similar manner to accomplish a similar purpose.

To facilitate an understanding of the principles and features of the embodiments of the present disclosure, example embodiments are explained hereinafter with reference to their implementation in an illustrative embodiment. Such illustrative embodiments are not, however, intended to be limiting.

The materials described hereinafter as making up the various elements of the embodiments of the present disclosure are intended to be illustrative and not restrictive. Many suitable materials that would perform the same or a similar function as the materials described herein are intended to be embraced within the scope of the example embodiments. Such other materials not described herein can include, but are not limited to, materials that are developed after the time of the development of the disclosed technology, for example.

Embodiments of the disclosed technology include an electronic inspection probing device with an integrated image capture device, capable of determining the condition of a wood structure. "Condition" as used herein may refer to any indicator of the state of the wooden structure, such as, as non-limiting examples, physical integrity, load carrying capacity, hardness, fiber strength, fiber integrity, the presence or absence of decay causing agents (e.g., fungi), grain, color, or open areas. In various embodiments, an electronic inspection device with an integrated image capture device, may enable the automated creation of a "profile" of the condition of the wood structure on which the device is used.

Throughout this disclosure, some embodiments are described in exemplary fashion in relation to an electronic inspection device for a wood structure. But embodiments of the disclosed technology are not so limited. In some embodiments, the disclosed technique may be effective in evaluating the condition of other wooden structures or objects, or structures or objects made of materials other than wood.

Referring now to the drawings, FIG. 1 depicts a side view of an example probing device 100 of an embodiment of the disclosed technology. The probing device 100 may include a horizontal handle 103, an electronics unit 105, a wireless transmitter 124, a distance sensor 104, a shaft 106, an electronics connector 114, an image capture device 108, and a probing tip 122. Although the handle is depicted in FIG. 1 as being horizontal, other orientations are envisioned as being within the scope of the disclosed technology. For example, the handle could be oriented at a non-zero angle with respect to the shaft. On the first end, a substantially rigid cylindrical shaft 106 may be connected to the electronics unit 105, which may include a wireless transmitter 124 that enables data acquired by the probing device to be transmitted to a remote computing device wirelessly. In some embodiments, the wireless transmitter 124 may have Bluetooth capability. The horizontal handle 103 may be attached to the electronics unit 105, and the shaft 106, such that the horizontal handle 103 may be parallel to the shaft, so that an operator may insert the probing device 100 into a hole in a wooden structure.

In some embodiments, the distance sensor 104 may be an optical distance sensor. For example, the distance sensor 104 may include a laser-light source and one or more optical sensors (e.g., optical distance measurement array). The laser-light source may be configured to emit a laser beam towards the structure 112 (e.g., substantially parallel toward the shaft 106), which reflects off the surface of the wooden structure 112. The one or more optical sensors receives a reflection of the laser-light source the and reflection is used to calculate or approximate a distance between the optical sensor and the structure 112. In some implementations, the distance sensor may include one or more image sensors, and may be configured to capture an image including the shaft 106 and/or the structure 112 and, through image processing, approximate a distance between the optical sensor and the structure 112. In some embodiments, the distance sensor 104 may be a short-range sonar instrument, which may emit sonar signals parallel to the shaft 106 that ping off a wooden structure back to the distance sensor to provide the distance between the distance sensor 104 and a structure being inspected. In certain embodiments, the distance sensor 104 may be a string potentiometer. As shown in FIG. 1, the angle of the distance sensor 104 may be adjusted by loosening a dial 107 on the side of the distance sensor 104, shifting the sensor up, and then tightening the dial to secure the distance sensor 104 at the adjusted angle. The distance sensor 104 may calculate a location of the image capture device 108 within a structure based on the distance to the structure, the angle between the distance sensor 104 and the shaft 106, and the length of the shaft 106 up to the image capture device 108.

On the second end of the shaft 106, an image capture device may be secured to the shaft 106. The shaft 106 may further include a probing tip 122 on the second end, which may, for example, slide over the image capture device 108, while continuing to permit the image capture device 108 to capture images (e.g., the probing tip 122 may be transparent in at least the area which covers a lens of the image capture device 108), or may connect to the shaft 106 adjacent the image capture device 108. The probing tip 122 and the substantial remainder of the shaft 106 may be made of metal, carbon fiber, plastic, fiberglass, other composite material, or combinations thereof. The probing tip 122 may be used to guide, align, or center the shaft within a hole bored in a wooden structure. The probing tip 122 may also be used to clean out debris in a bored hole. The image capture device 108 may be connected to an electronic connector 114 incorporated into the shaft 106. In this embodiment the electronic connector 114 may be a connector which electrically connects image capture device 108 to electronics unit 105. The connector 114 may be electrically connected to the electronics unit 105, including the wireless transmitter 124, which may transmit the acquired image data and the location data to a computing device for further processing. Alternatively, or in addition to transmitting the data, the image data and location data may be automatically displayed on a visual display attached to the probing device 100, for example on the side of the electronics unit 105 or on top of the distance sensor 104. In some embodiments, the visual display may be an LCD or OLED display, which may also be used to show operating instructions.

Figure 2:
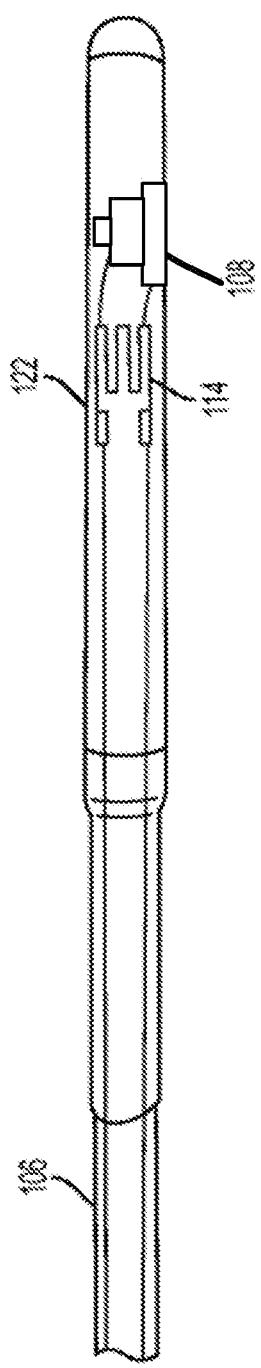

FIG. 2 depicts a close-up of the second end of an example device of an embodiment of the disclosed technology, where the shaft 106 may comprise a probing tip 122 that may surround the image capture device 108. The probing tip 122 may be slightly larger in diameter than the substantial length of the shaft 106. For example, the probing tip 122 may have a diameter of about 0.35 inches and the main portion of the shaft 106 may have a diameter of about 0.30 inches. The probing tip 122 may fit over the image capture device 108 and may be secured to the remainder of the shaft 106 by a fitted adhesive sleeve, though any securing mechanism may be used. The probing tip 122 may be conically shaped for self-alignment within inspection hole 160. The electronic connector 114 may be wired to the image capture device 108 and relays image information that the image capture device 108 captures at each location to the electronics unit 105 at the base of the shaft 106. The image information may be processed to determine a wood condition at each location (e.g., hardness).

Figure 3:
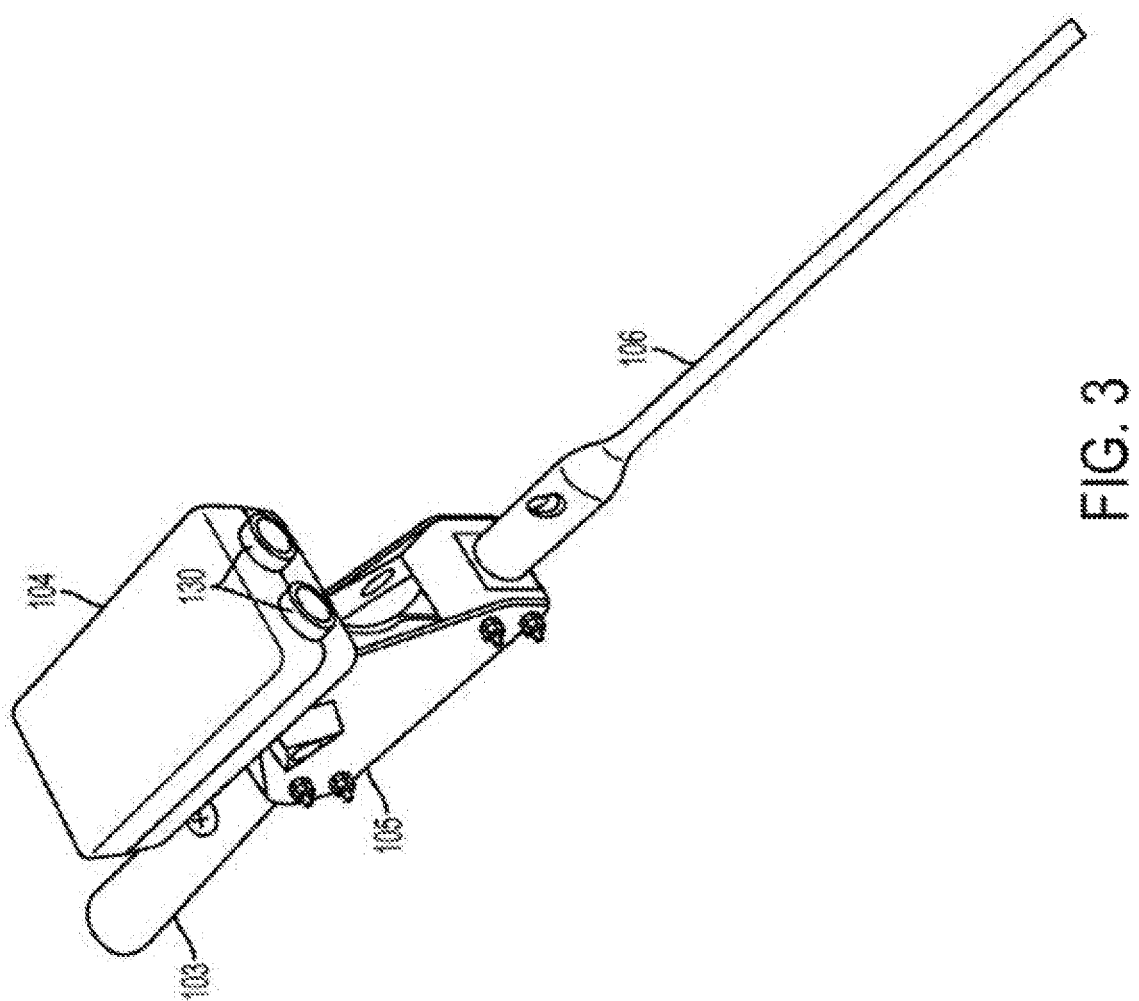

FIG. 3 depicts a close-up of the first end of an example device of an embodiment of the disclosed technology, wherein a distance sensor 104, a horizontal handle 103, and an electronics unit 105 may be attached to the shaft 106. The distance sensor 104 may have two sound transmitters/receivers 130 facing in the direction of the shaft 106. The distance sensor 104 may have a power button to activate the device and may be battery-operated.

Figure 4:
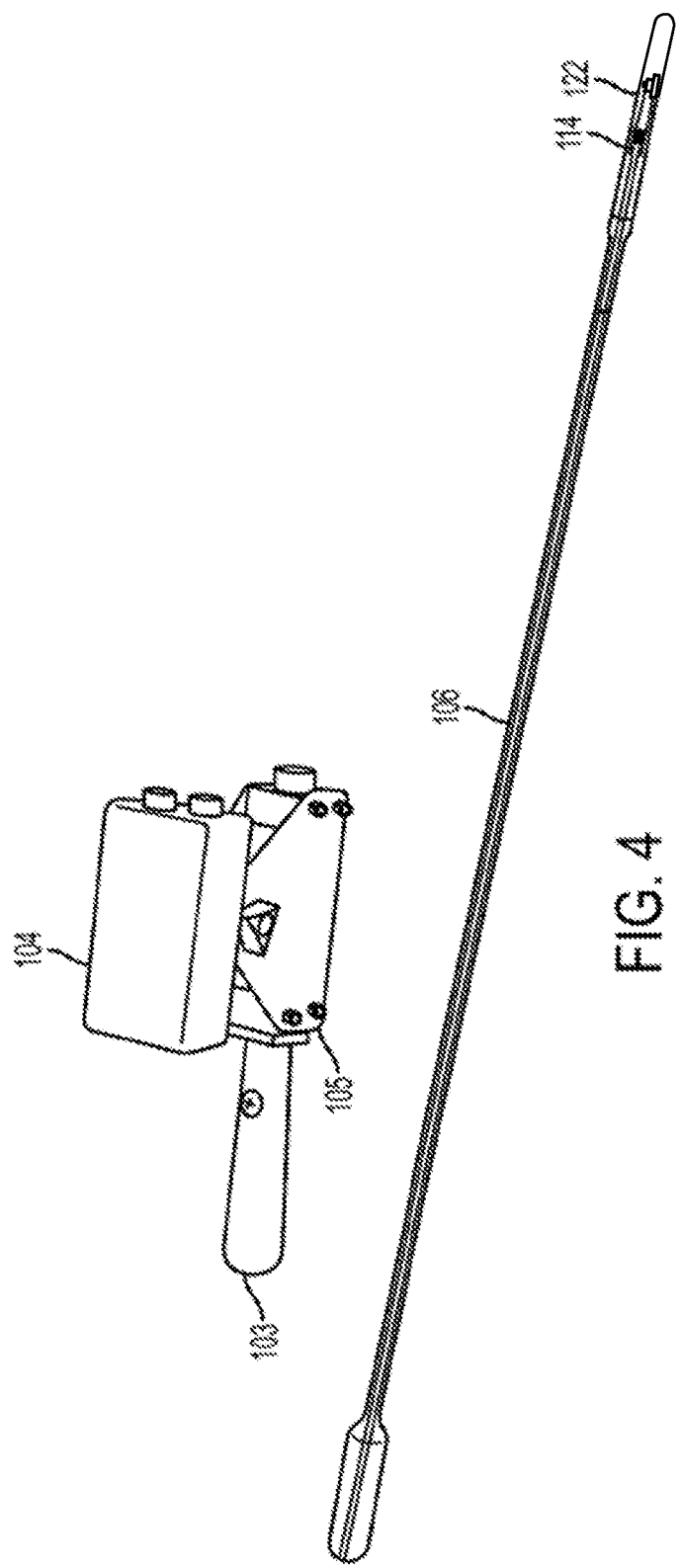

FIG. 4 depicts an example device of an embodiment, with the shaft 106 removed from the electronics unit 105, distance sensor 104, and horizontal handle 103. The shaft 106 may be removed to facilitate transport of the probing device 100, to switch out shafts of different lengths or diameters, and/or for additional consideration, depending on the intended inspection hole and structure. In this example, the base of the shaft 106 may have a larger diameter than the rest of the shaft 106, including the probing tip 122, to support the mechanical connection between the shaft 106 and the electronics unit 105.

Figure 5:
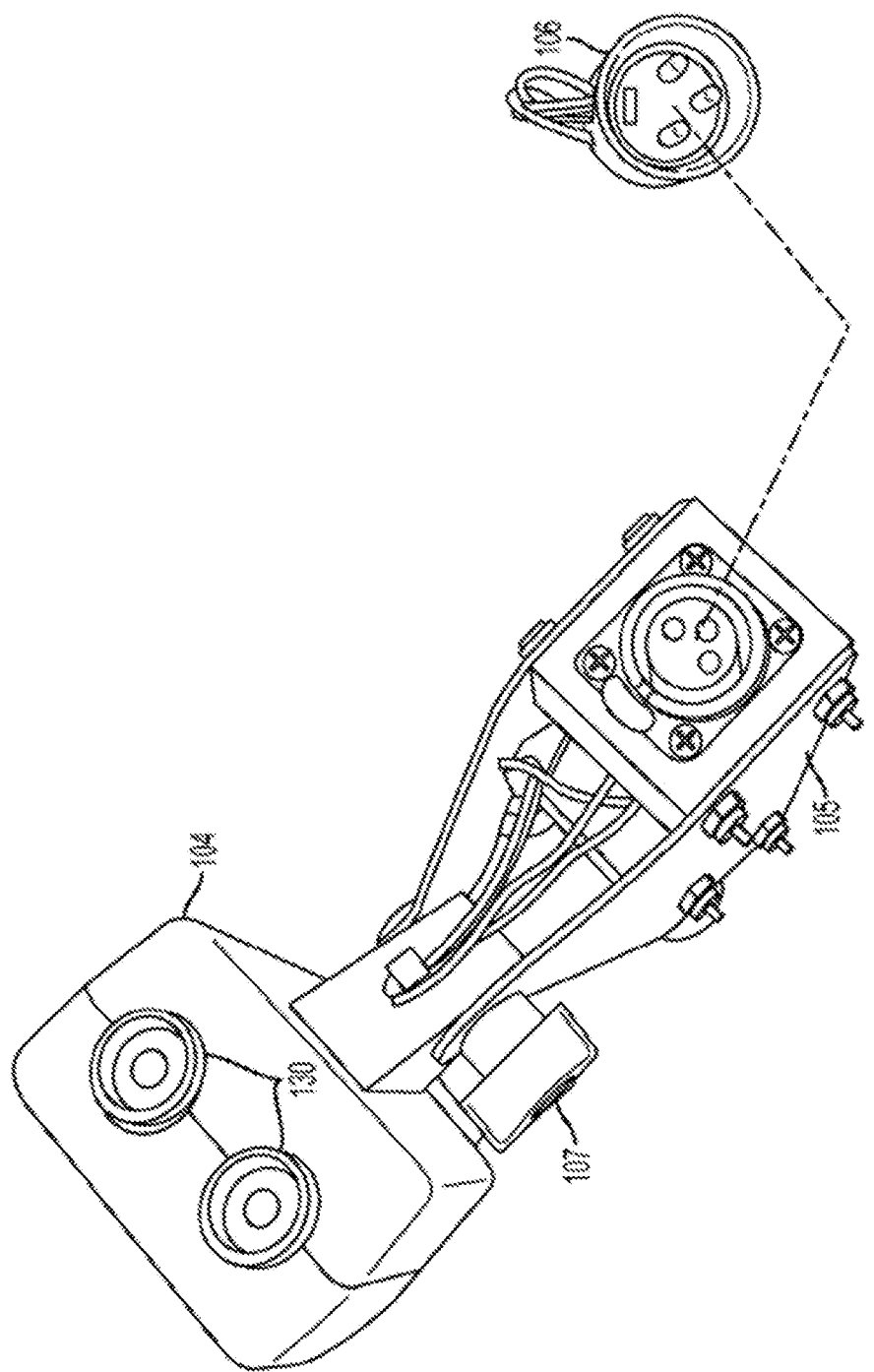

FIG. 5 depicts a connection between the removable shaft and the electronics unit 105. The enlarged base of the shaft 106 may be fitted to snap into the electronics unit 105, and the three metal prongs provide the electrical connections between the components in the shaft 106 (e.g., the image capture device) and the electronics unit 105. The two transmitters/receivers 130 of the distance sensor 104 are shown, as is the dial 107 permitting adjustment of the angle of the distance sensor 104.

Figure 6:
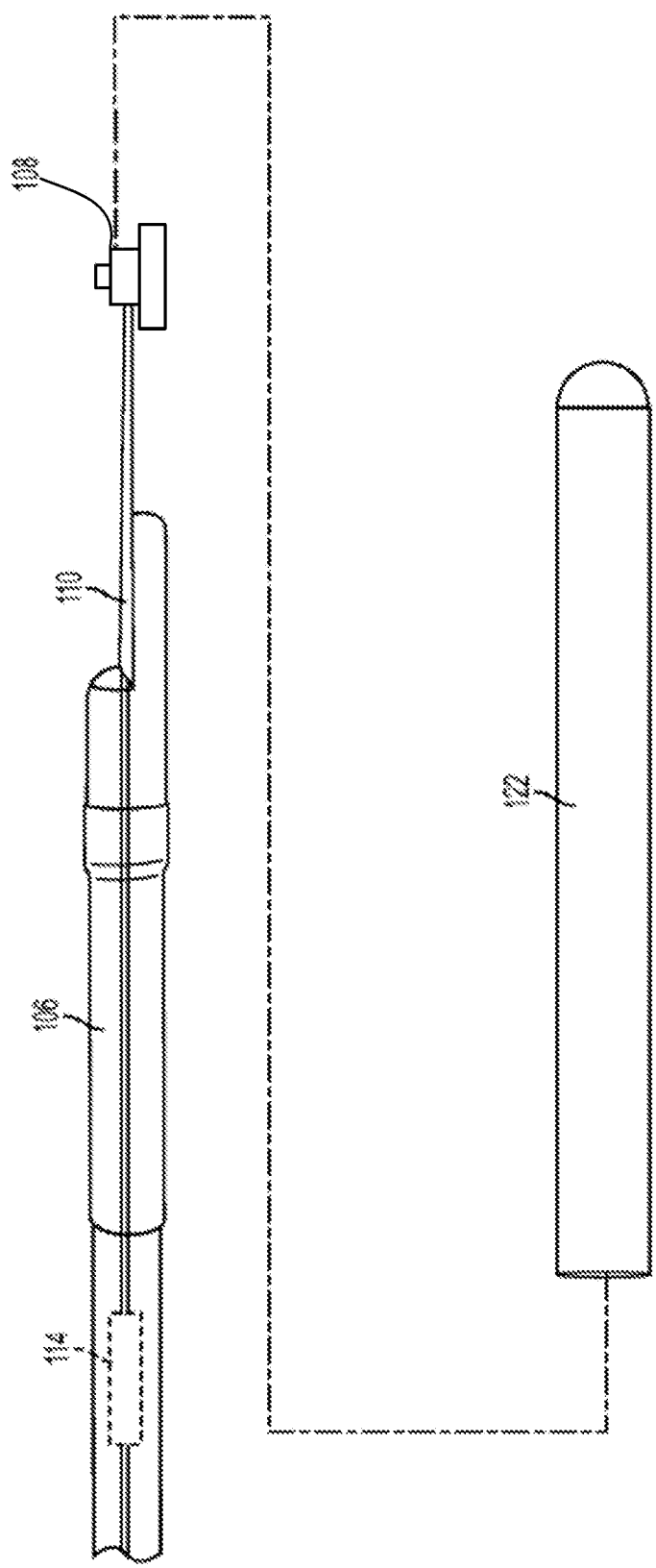

FIG. 6 depicts how a probing tip 122 may be removed from and reattached to the shaft 106. In this embodiment, the image capture device 108 may be secured to the shaft using support structure 110, which in this embodiment may comprise a rigid metal strip. The electronic connector 114 may be wired to the image capture device 108 and relay the data (e.g., image data) acquired by image capture device 108 of the wood at each location.

Figure 7:
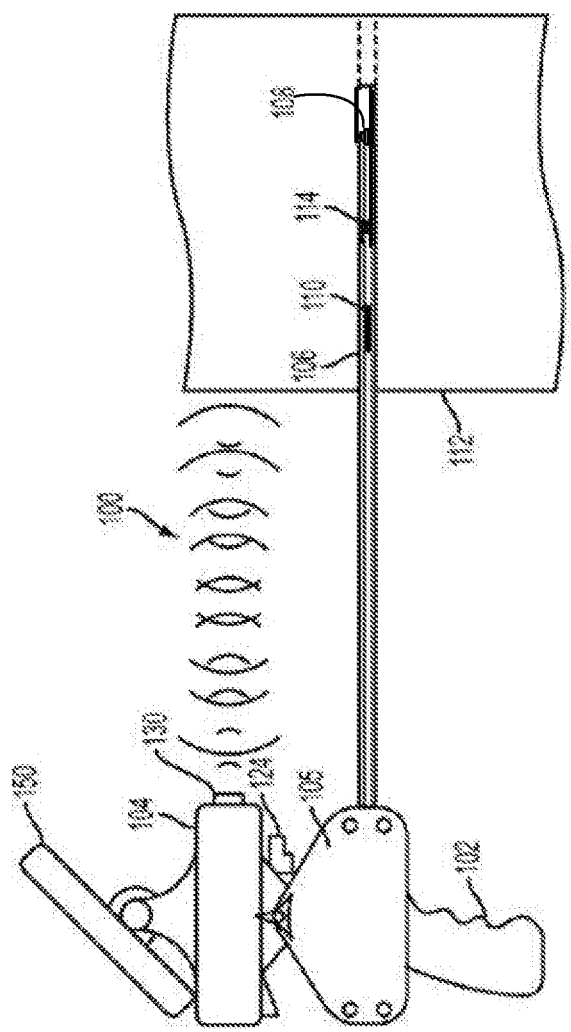

FIG. 7 depicts a side view of an example device of an embodiment of the disclosed technology in operation. The probing device 100 is shown inspecting the condition of a wooden structure 112. The distance sensor 104 may be powered on and then sends a sonar signal off the surface of the wooden structure 112, which may then be reflected back and received by the distance sensor 104. The end of the shaft 106 closest to the image capture device 108 may be inserted into a bored hole in the wooden structure 112. The distance sensor 104 may determine the location of the image capture device 108 using a calculation based on the distance between the transmitter/receiver 130 of the distance sensor 104 and the wooden structure 112, the length of the shaft 106 up to the image capture device 108, and the angle between the distance sensor 104 and the shaft 106. The location and image data from the inspection may be stored in the electronics unit 105, visually displayed on the device using visual display 150, and/or transmitted to a remote computing device, using the wireless transmitter 124. In this embodiment, the vertical handle 102 may be not parallel to the shaft 106.

Figure 8:
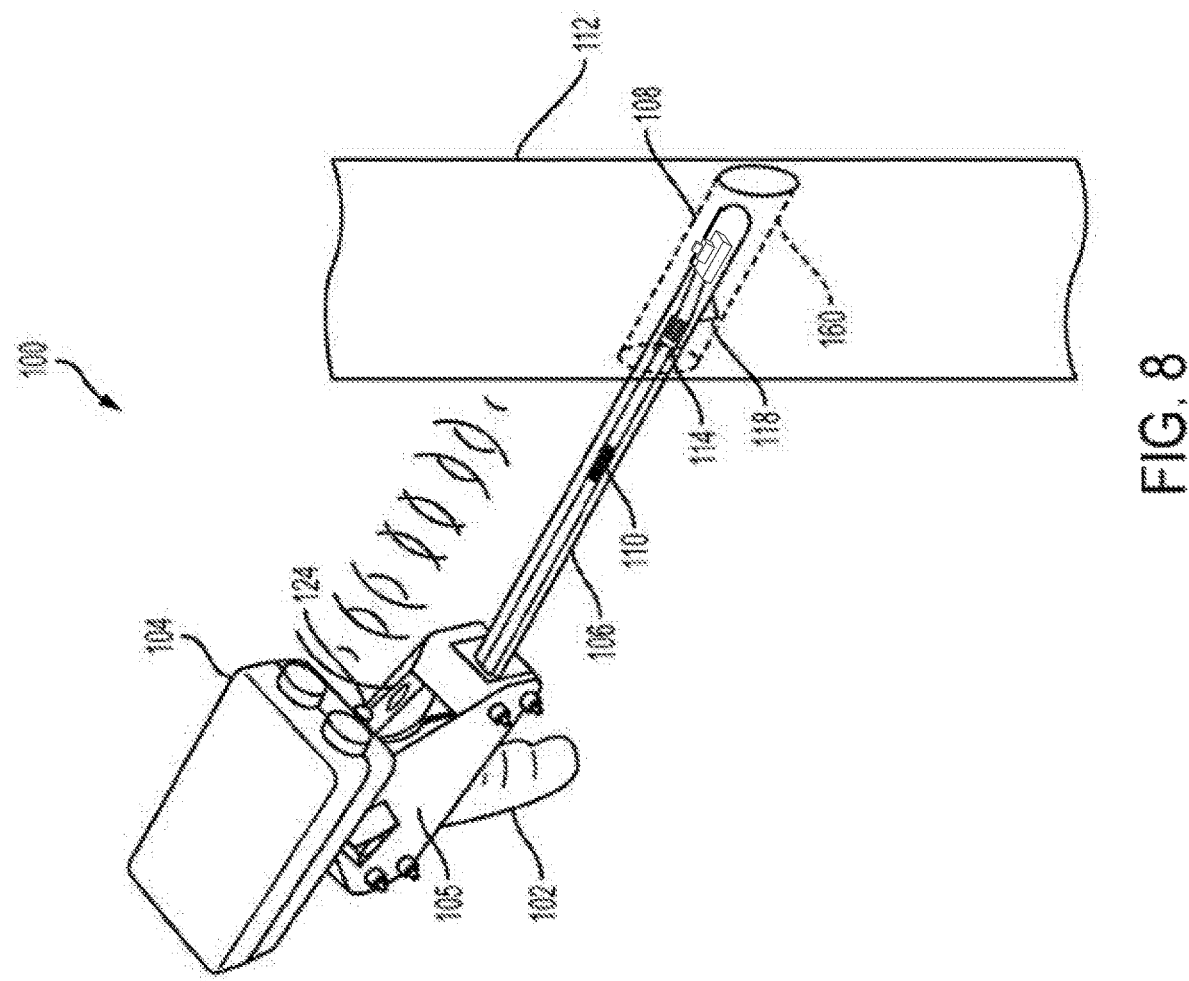

FIG. 8 depicts an angled view of an example device of an embodiment of the disclosed technology having an image capture device. When inserted into a bored hole, the distance sensor 104, in conjunction with a processor in the electronics unit 105, may determine the location of the image capture device 108 within the wooden structure 112. The image capture device 108 may be connected to a support structure 110 and an electronics connector 114.

FIG. 9 depicts a distance sensor 104 at a non-zero angle to the shaft 106 of an embodiment of the disclosed technology. This example configuration may be useful in inspecting the condition of portions of a wooden structure 112 below the ground-line 170. The distance sensor 104 may calculate the location of the image capture device 108 within the wooden structure 112 using the distance provided by the sonar signal, the length of the shaft 106 up to the image capture device 108, and the angle between the sonar signal of the distance sensor 104 and the shaft 106.

Figure 10A:
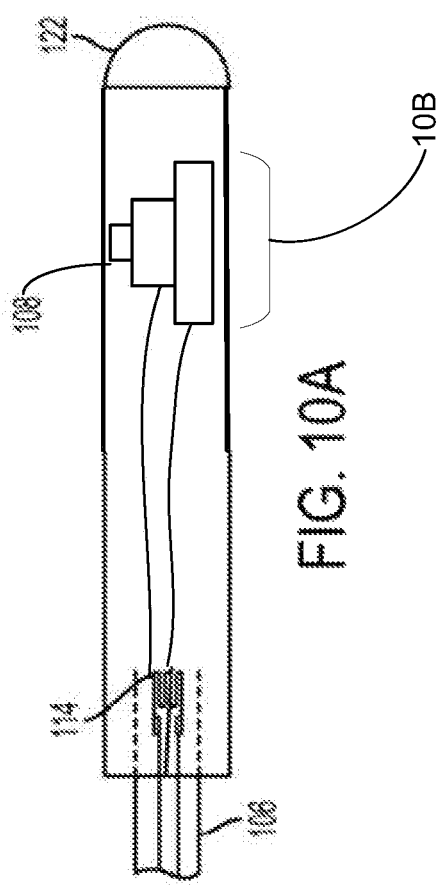
FIGS. 10A and 10B depict an example image capture device within a shaft of an example device according to an example embodiment of the disclosed technology.
Figure 10B:
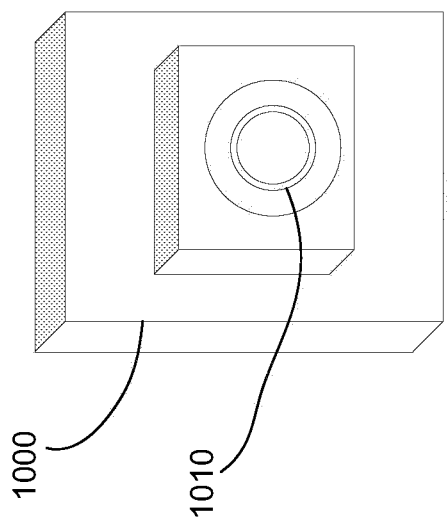

FIGS. 10A and 10B depict an image capture device 108 near the end of shaft 106 according to an example embodiment of the disclosed technology. In FIG. 10A, the probing tip 122 end of the shaft 106 is shown. FIG. 10B shows a cross-sectional view of the area indicated as 10B in FIG. 10A viewed from the end of the probing tip 122, and depicts an example image capture device 108. Other types or configurations of one or more image capture sensors or devices may be used. When the image capture device 108 may be inserted into a bored hole of a wooden structure, the image capture device 108 may capture images of the interior surfaces of the wooden structure. In some embodiments, image capture device 108 may be equipped with various lenses, sensors, and light sources, allowing for the capture of image data of various types. For example, image capture sensors capable of receiving wavelengths beyond the visible spectrum may be utilized. Additionally, in some embodiments, one or more illumination sources may be utilized, in order to illuminate the surface toward which the image capture device 108 is oriented. In some embodiments, the illumination may include, as non-limiting examples, light-emitting diodes (LEDs), a laser light source, or some other form of electromagnetic wave emitters. According to some embodiments, the light source may include one or more integrated white LEDs, with a strong emission range in the wavelength region around 450 nm, and a broad emission range between 500 and 650 nm. In some embodiments, one or more dyes (e.g., fluorescent dyes) may be applied prior to capturing an image (e.g., during or after boring into the wood). In some cases, these dyes may interact with the wood and respond to specific wavelengths emitted by the light source (e.g., to better identify certain organisms present in the wood, and/or to better identify heartwood). In the example embodiment in FIG. 10B, the image capture device 108 may have a lens assembly 1010 which may be attached to a printed circuit board (PCB) and drive circuitry 1000. The image capture device 108 may include one or more image sensors, configured to interpret light impulses received through the lens assembly 1010. The one or more image sensors may be embedded with the PCB and drive circuitry 1000.

FIGS. 11A and 11B depict an example system of an embodiment of the disclosed technology for evaluating the condition of a wooden structure. The system may include a probing device 100, a wooden structure 112, an operator 120, and a computing device 116. The wooden structure 112 may include an inspection hole 160, which may be pre-drilled or drilled by the operator 120 or other individual during the inspection. The probing device 100 may then be inserted into the wooden structure 112 by way of inspection hole 160. The probing device 100, via the image capture device 108, may capture image data of the interior surfaces of the wooden structure as the probing device 100 may be moved through the inspection hole 160. The data obtained by the probing device 100 may then be transmitted to a computing device 116, via a physical connection or download as shown in FIG. 11A, or wirelessly as shown in FIG. 11B. The computing device 116 may then sort and analyze the data to provide a condition profile of the wood surrounding the inspection hole 160, or multiple inspection holes, within the wooden structure 112, to determine whether the wooden structure 112 requires any immediate or future remedial treatment, reinforcement, or replacement.

Figure 12:
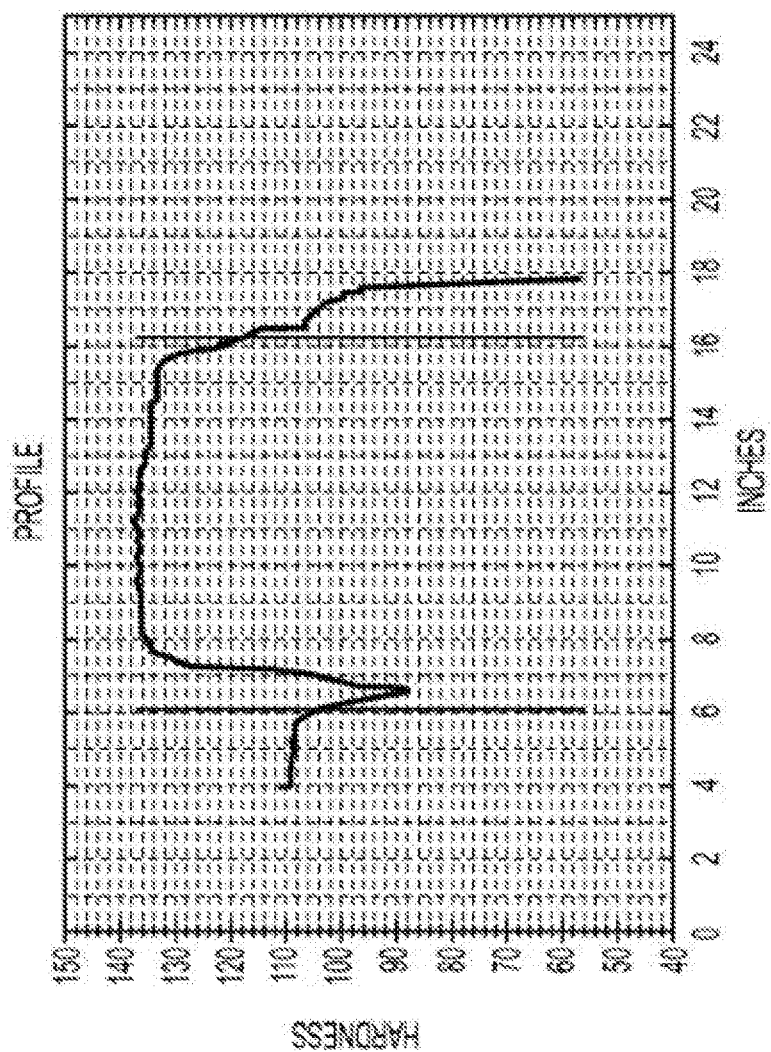

FIG. 12 illustrates an example condition (hardness) plot generated by an embodiment of the disclosed technology, depicting a hardness indicator versus distance into the inspection hole 160. In some embodiments, other forms of visual indicators may be generated, such as a table with text notes to indicate the specific form of defect or condition indicator found at a given distance.

Figure 13:
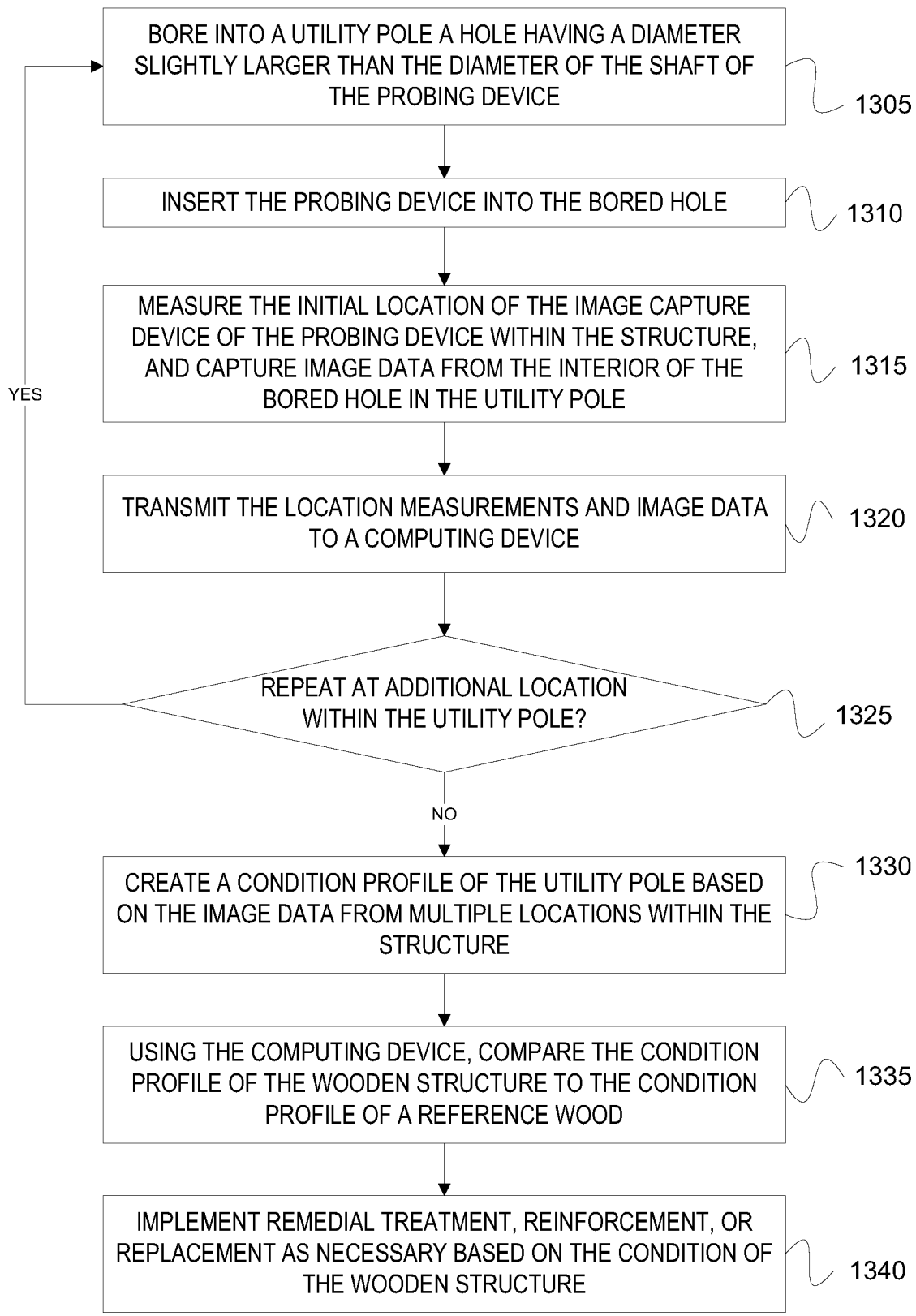

FIG. 13 depicts a flow chart outlining steps of an example method utilizing an embodiment of the disclosed technology to assess and maintain a utility pole. Initially, a user may bore 1305 a hole 160 into a utility pole. The bored hole 160 may have a diameter that is slightly larger than the shaft 106 of the probing device 100. In some cases, the probing device 100 may include a boring element and may be used to bore 1305 the hole 160. According to some embodiments, a hole 160 may be pre-bored, and boring a hole 1305 may be omitted. After boring the hole 160, a user may insert 1310 the probing device 100 (or a shaft 106 of the probing device 100) into the bored hole 160. The probing device 100 measures 1315 the initial location of the image capture device 108, and captures image data from the interior surfaces of the bored hole 106. The location and image data are then transmitted 1320 to the computing device 116. If additional information is desired, the boring 1305, inserting 1310, measuring and capturing 1315, and transmitting 1320 may be repeated 1325—Yes. In some cases, gathering data as multiple locations within the utility pole may help create a more complete understanding (e.g., a condition profile) of the condition of the utility pole 1325.

Once the data is gathered 1325—No, computing device 116 may create 1330 a condition profile of the utility pole based on the collected image and location data. Then, the computing device 116 may compare 1335 the condition profile of the utility pole to the condition profile of a reference wood, in order to ascertain the condition of the utility pole. Based on the ascertained condition of the utility pole a user may implement 1340 remedial treatment, reinforcement, or replacement as necessary. In some cases, computing device 116 may automatically recommend remedial treatment, reinforcement, or replacement based on the condition. In certain instances, computing device 116 may automatically initiate remedial treatment, reinforcement, or replacement based on the condition (e.g., by ordering or requesting certain materials, automatically preparing work orders, and/or tagging (e.g., geo-tagging) the utility). In some embodiments, computing device 116 may determine and/or recommend a treatment agent or methodology based on, for example, a type, amount, and/or location of decay observed. For example, if internal decay is observed, fumigant application may be determined, whereas if shell rot is observed, a copper naphthenate application may be determined. In some cases, the computing device 116 may determine and/or recommend reinforcement or replacement strategy (e.g., immediate replacement or truss-type reinforcement) based on, for example, a type, amount, and/or position of observed decay or degradation.

In some embodiments, the method depicted in FIG. 13 may be combined with other inspection methods to provide additional inspection of a wooden structure or verification of other forms of inspection. According to some embodiments, the method described in FIG. 13 may omit 1325 and be applied a single time. One of ordinary skill will understand that this is merely an example, and one of ordinary skill would understand that various changes, additions, and omissions are within the scope of the present disclosure.

Figure 14:
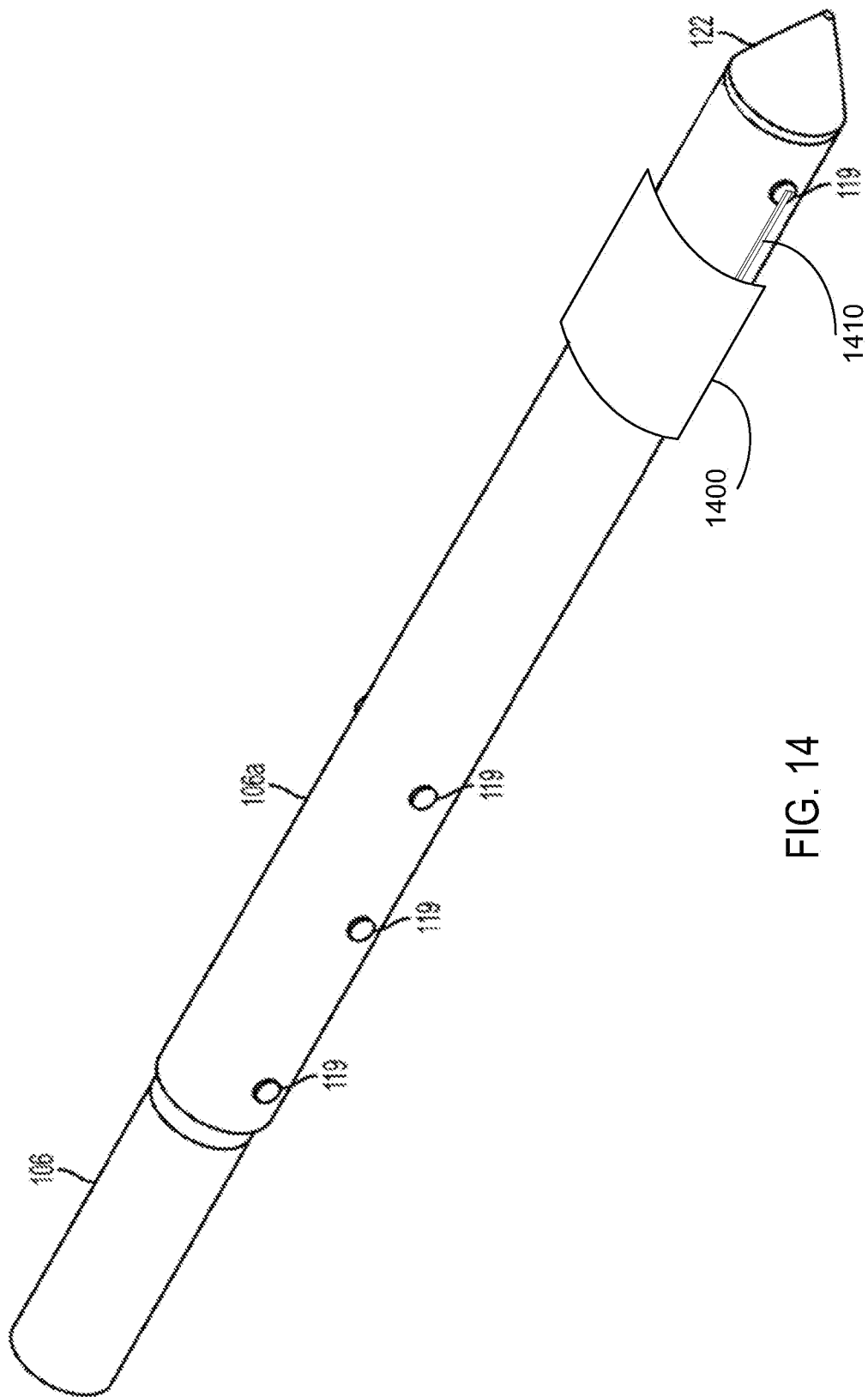
Figure 15:
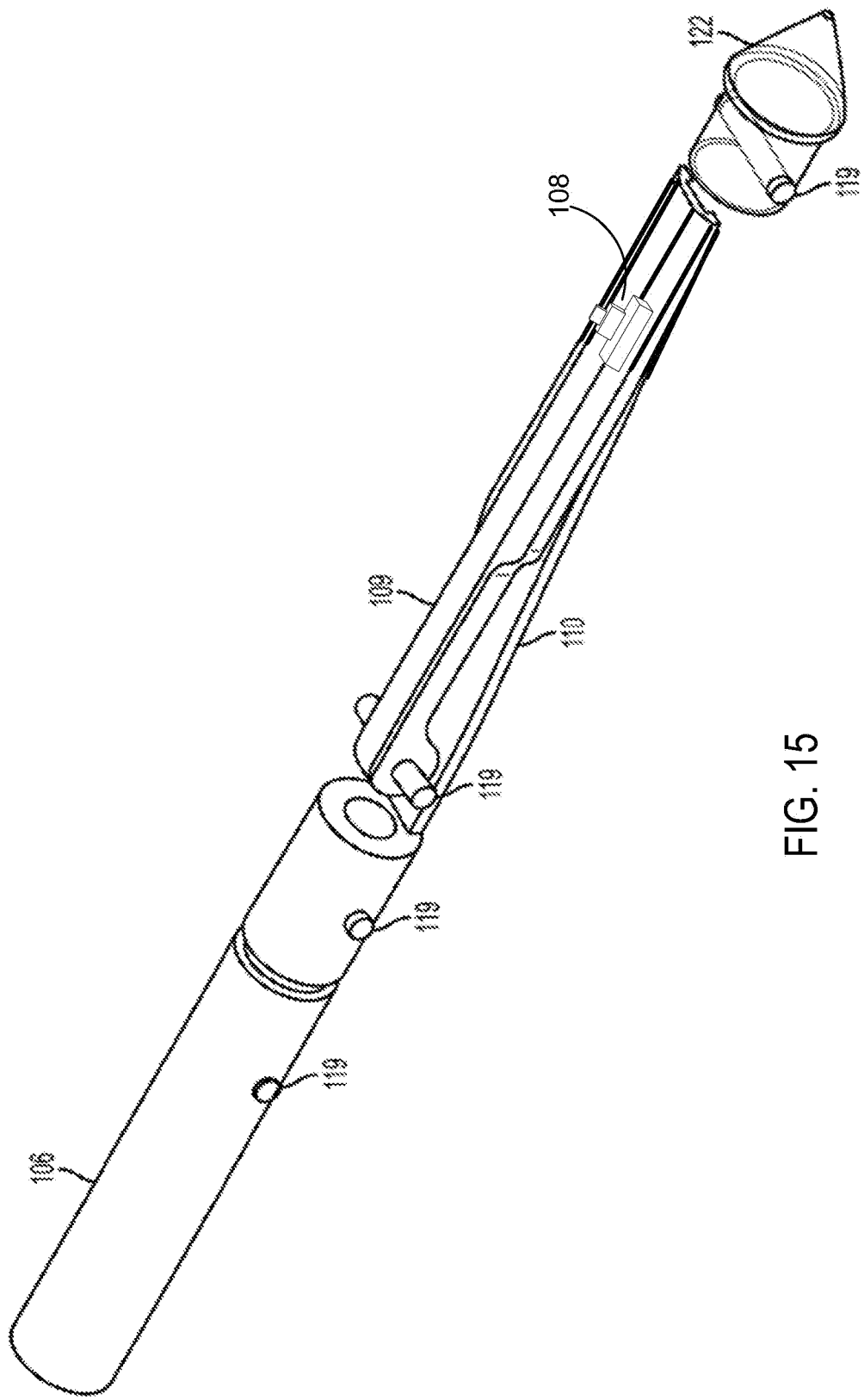

FIGS. 14-15 depict the assembly of one end of an example device of the disclosed technology. FIG. 14 shows an external view of the assembly, wherein the shaft 106 may comprise a tube 106a and a probing tip 122. The probing tip 122, which may have a conically shaped end, may be secured to one end the tube 106a, and the other end of the tube 106a may be secured to the substantial remainder of the shaft 106. The tube 106a may fit over the image capture device 108, and the probing tip 122 may be adjacent to the image capture device 108. The probing tip 122 also has a slot for wood particles to be removed. In this embodiment, multiple pins 119 may be used to secure components of the device together. Attached to the pin 119 closest to the probing tip 122 may be a support member 1410, which may allow lens cover 1400 to retract when the probe is being pulled out of the wooden structure, which may expose image capture device 108 so that image capture device 108 may collect data. In some embodiments, lens cover 1400 is opaque to the wavelengths capturable by image capture device 108. FIG. 15 depicts the assembly shown in FIG. 14, wherein the tube 106a portion of the shaft 106 has been removed. The image capture device 108 may be secured to attachment structure 109, which may be secured to the shaft by a pin 119 that slides through a fitted hole on the end of the attachment structure 109 opposite the image capture device. The image capture device 108 and the attachment structure 109 sit atop a support structure, which may be the metal strip 110 in this embodiment.

Figure 16:
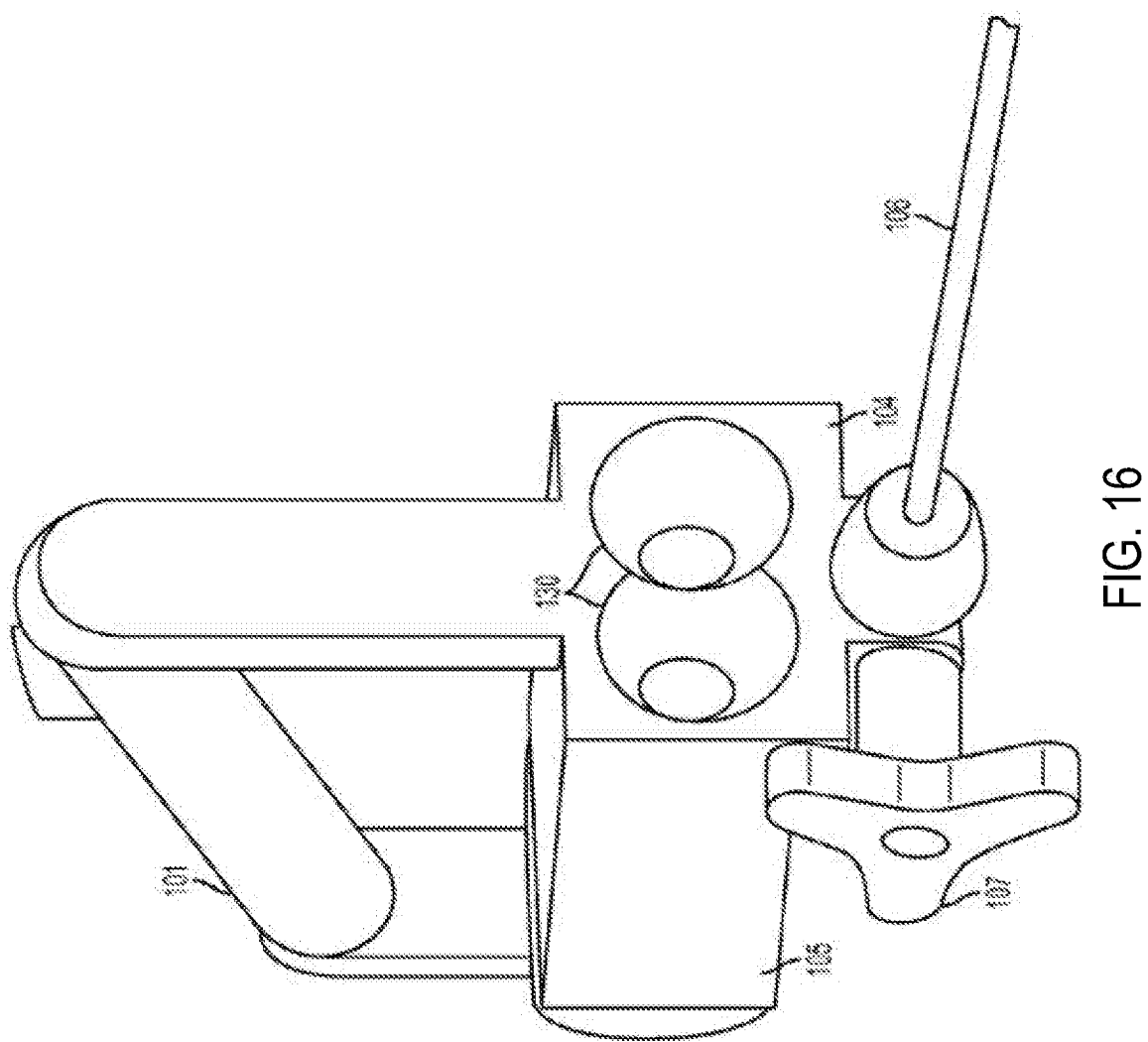
Figure 17:
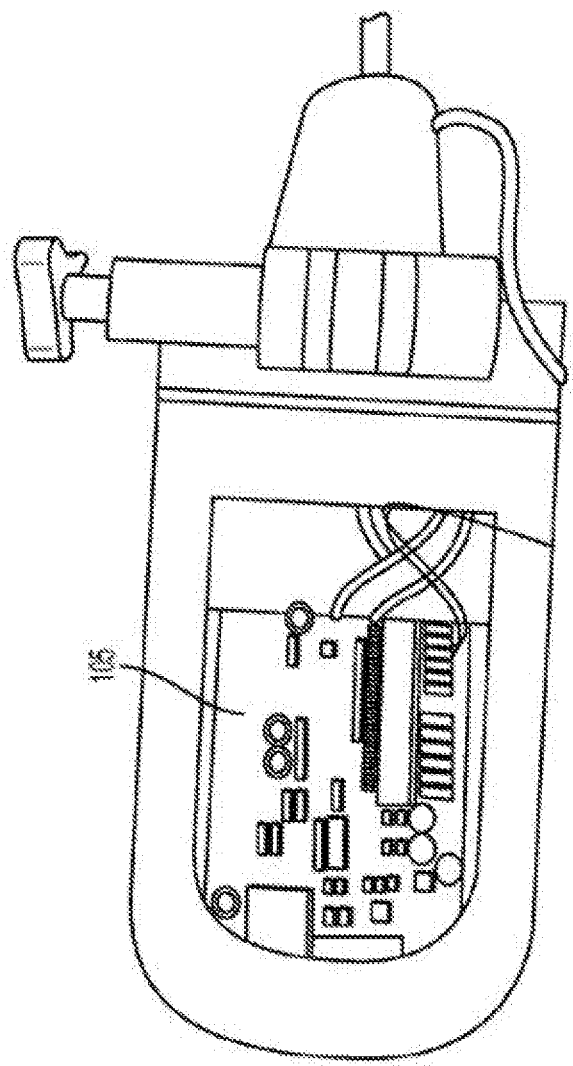

FIG. 16 depicts an end of an example device of an embodiment of the disclosed technology, wherein a distance sensor 104, a raised handle 101, an electronics unit 105 and a dial 107 may be attached to the shaft 106. FIG. 17 depicts how the housing of the electronics unit 105 may be opened to allow electronics access, for example, by a field operator after inspecting a utility pole. The housing of the electronics unit 105 may be made of plastic, fiberglass, or more preferably metal, and in some embodiments the housing and the raised handle 101 may be manufactured using 3-dimensional printing. In some embodiments, electronics unit 105 may not be integrated with the device, but may be remotely connected to the device. In some embodiments, electronics unit 105 may be able to house a removable storage medium, which may be used to store images from the image capture device or store operating firmware for the electronics unit 105. According to some embodiments, the electronics unit 105 may contain a power source, such as a rechargeable battery. In some embodiments, the power source may be located externally. In some embodiments, the power source may be an array of solar cells. In some embodiments, electronics unit 105 may contain software to enable to the processing and/or transmission of image data. According to some embodiments, electronics unit 105 may contain software to categorize image data according to a trained model.

Figure 18:
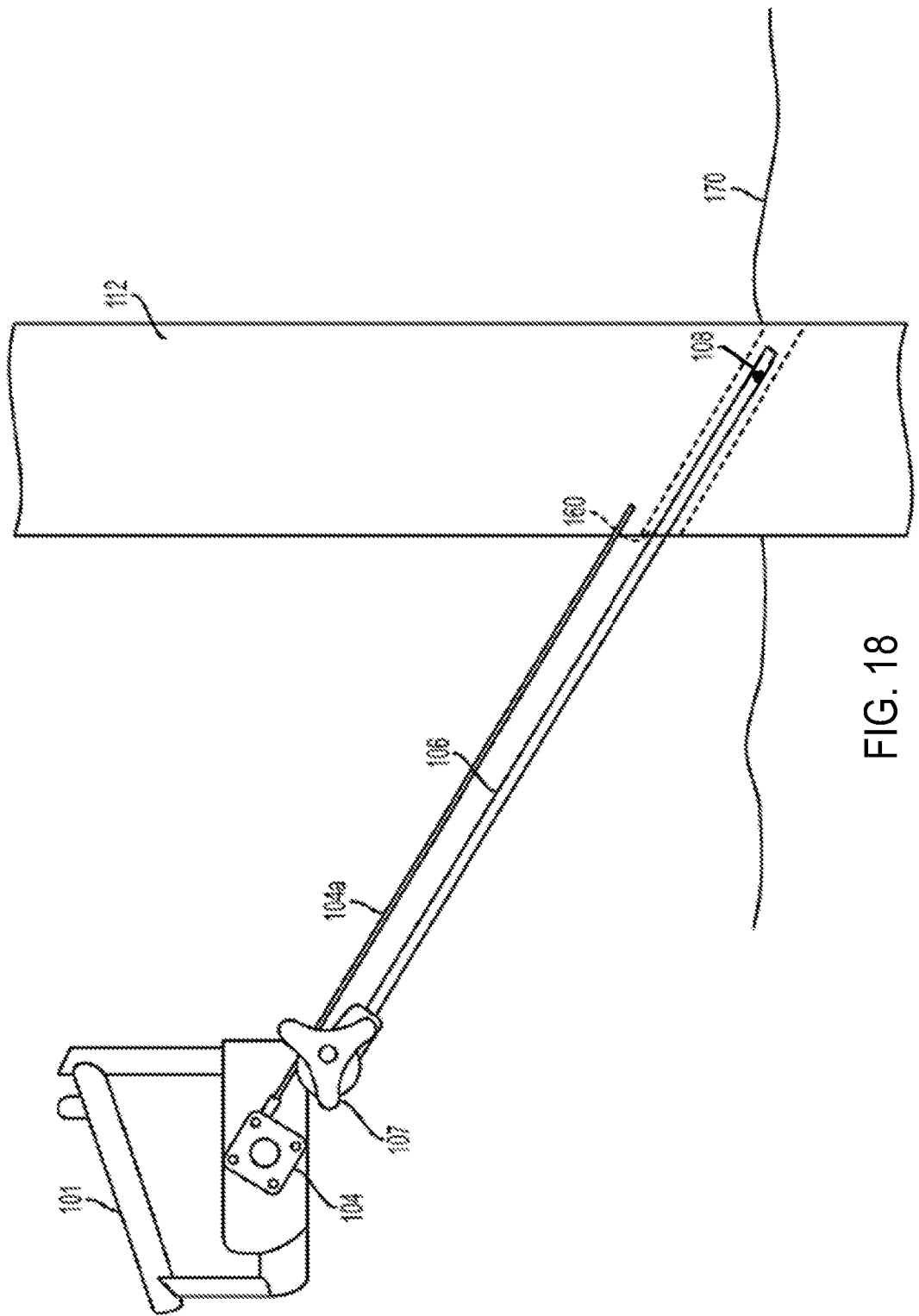

FIG. 18 depicts a side view of an example device of an embodiment of the disclosed technology, wherein the distance sensor 104 is a string potentiometer, and the shaft 106 may be angled downward to inspect the area of a wooden structure 112 below ground-line 170. The angle of the shaft to the ground-line may be measured using an inclinometer in this embodiment. By utilizing the probe in the angled manner illustrated in the example embodiment in FIG. 18, a three-dimensional understanding of voids may be ascertained, as opposed to inserting the shaft 106 exactly horizontally (that is, there is no variation of probe position with respect to the height of pole 112) through pole 112, where such an understanding would not be possible. The string potentiometer determines the distance that the image capture device 108 has traveled within the wooden structure 112 using a cable or string tethered to a stable support, for example, the wooden structure. As the image capture device 108 moves further into the structure, the corresponding movement of the cable produces a voltage range, which may be converted from an analog signal, in this case variable voltage, to the digital output, in this case distance, using an analog-to-digital converter, and the digital output may be recorded. Using the distance measured by the string potentiometer and the angle of the shaft measured by the inclinometer, the location of the image capture device 108 within the structure may be automatically determined. In some embodiments, the angle measured by the inclinometer is with respect to the horizontal plane, typically perpendicular to the vertical axis of the pole. In some embodiments, the integrated inclinometer may be replaced by a secondary inclinometer.

Figure 19:
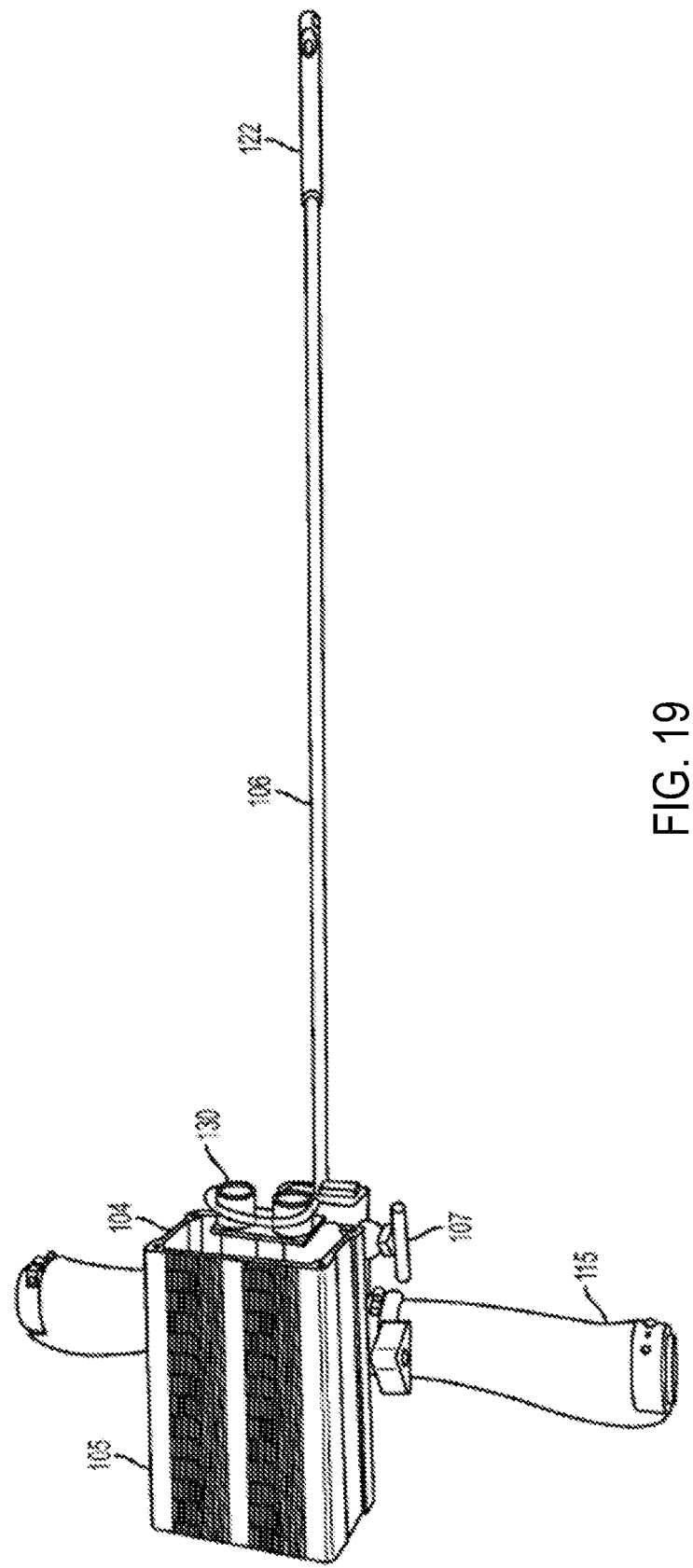

FIG. 19 depicts an overhead view of an example device of an embodiment of the disclosed technology, wherein the distance sensor 104 may comprise a sonar instrument with two sound transmitters/receivers 130 facing in the direction of the shaft 106. The device may further comprise an electronics unit 105 within a metal housing attached to the shaft 106. In this embodiment, the dual-grip handle 115 may comprise two rubber grips, one on each side of the shaft 106, which may permit a user to operate the device with two hands to ensure careful and stable insertion of the probing tip 122 into and through a hole in a wooden structure.

Figure 20:
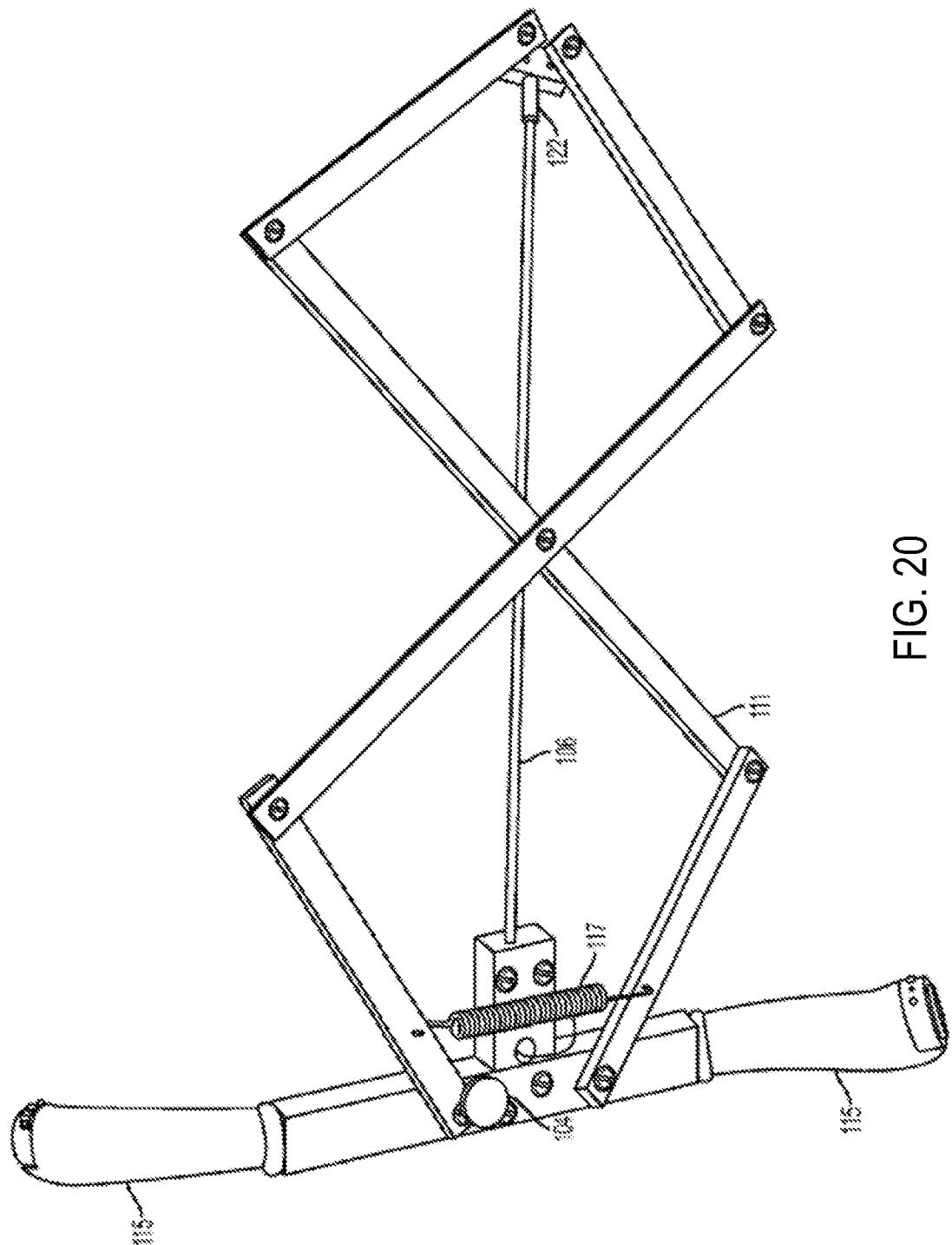

FIG. 20 depicts an overhead view of a distance sensor 104, which in this embodiment may comprise a potentiometer connected to collapsible scissors 111. The collapsible scissors 111 may be bolted to the base of the shaft 106 and may be expanded along the length of the shaft 106 up to the image capture device 108 using a spring 117. When the probing tip 122 of this embodiment is inserted into a wooden structure, the collapsible scissors 111 may press against the surface of the wooden structure and fold back towards the base of the shaft 106 in a magnitude corresponding to the distance that the image capture device 108 has traveled into the wooden structure. A potentiometer may be connected to the collapsible scissors 111. In this illustration, the potentiometer may be connected to the end of the collapsible scissors 111 opposite the probing tip 122. The potentiometer may rotate as the collapsible scissors 111 fold back towards the base of the shaft 106 and may output a variable voltage corresponding to the degree of rotation. The variable voltage may be then correlated to the distance or location of the image capture device 108 in the wooden structure. In this embodiment, a spring 117 may be secured to the collapsible scissors 111 so that the collapsible scissors 111 may fold back according to the movement of the shaft 106 into a hole in a wooden structure. The tension of the spring 117 may be optimized to ensure accurate and repeatable distance or location measurements. As the probing tip 122 moves forward through a hole in a wooden structure, the collapsible scissors 111 may be folded or compressed between the base of the shaft 106 and the wooden structure. An inclinometer may also be used in conjunction with the collapsible scissors 111 and the potentiometer to determine the location of the image capture device 108 within a wooden structure.

FIG. 21 depicts a side view of a distance sensor 104, which in this embodiment may comprise a potentiometer and a compression sleeve 113 around the shaft 106. The compression sleeve 113 may comprise an elongated spring affixed to the base of the shaft 106 and expanded along the length of the shaft 106 up to the image capture device 108. A stop wire 121 may be secured to the dual-grip handle 115 and the end of the compression sleeve 113 closest to the image capture device 108 to prevent the compression sleeve 113 from extending beyond the end of the shaft 106. The potentiometer may have a string or cable 104a attached to the end of the elongated spring closest to the image capture device 108, or attached to an encasement around the elongated spring. When the image capture device 108 is inserted into a hole 160 in a wooden structure 112, the compression sleeve 113 may press against the surface of the wooden structure 112 and compress back towards the base of the shaft 106 in a magnitude corresponding to the distance that the image capture device 108 has traveled into the wooden structure. The string or cable 104a of the potentiometer may recoil into the potentiometer as the compression sleeve 113 compresses back toward the base of the shaft 106. The potentiometer may output a variable voltage corresponding to the movement of the string or cable 104a. The variable voltage may be then correlated to the distance or location of the image capture device 108 in the wooden structure 112. The tension of the elongated spring in the compression sleeve 113 may be optimized to ensure accurate and repeatable distance or location measurements. As the image capture device 108 and/or probing tip 122 moves forward through a hole 160 in a wooden structure 112, the compression sleeve 113 may be compressed between the base of the shaft 106 and the wooden structure 112. An inclinometer may also be used in conjunction with the compression sleeve 113 and the string potentiometer to determine the location of the image capture device 108 within a wooden structure 112.

Overview of the Devices, Systems and Methods of the Disclosed Technology

Changes in the appearance of the interior of a wooden structure are often indicative of the condition of that structure. For example, decay and decomposition of a wooden structure alter the structure of the wood and compromise the condition of the structure (e.g., reduce the hardness of the structure), as compared to normal wood (for example, no decay and decomposition or mechanical damage). As used herein, the term "wooden structure" refers to a structure comprising wood, such as, but not limited to utility poles. Moisture penetration into a wooden structure (one indicator of pre-decay) also alters the condition of the wooden structure, compared to a dry reference, which may impact the condition of the wood. The condition of a wooden structure may be determined by observing the appearance of the interior surfaces of the wooden structure by way of an image capture device.

The example probing devices, systems, and methods of the instant disclosed technology may be used to evaluate the condition of a wooden structure, by internally observing the visual condition of wood, by an image capture device, as interpreted by a computer model trained using machine learning, which helps indicate the condition of wood at a given location. Condition profiles may be assessed by conducting such measurements and recordings at various locations within the structure. The condition or strength of a wooden structure may be assessed by comparing the captured image data with a "reference" model, which are models generated by systems "trained" on a set of reference images, using machine learning. As would be understood by those of skill in the art, various machine learning techniques may be utilized to "train" a computer model, which may be used to categorize and thus recognize the condition of various wooden structures. As described in greater detail below, wooden structures may on occasion comprise voids or pockets of air. The probes and devices of the disclosed technology aid in the detection of voids or pockets in the wooden structures by noting the wood condition (e.g., the lack of density) in a particular portion or region of the wood based on internal-visual inspection. In particular, the trained system will categorize the wood on the basis of whether it includes voids, decay, solid wood, or soil. The devices, systems, and methods of the disclosed technology allow users to repeatedly and accurately profile the condition of wooden structures without the need for specialized and expensive drilling equipment.

The example probing devices, systems, and methods of the instant disclosed technology may be used to detect distinct conditions in a wooden structure, including sound wood, incipient decay, and advanced decay. The term "incipient decay" as used herein refers to an early stage of the decay process where the wood fibers have begun to lose strength but the decay has not proceeded far enough to evidently soften or otherwise perceptibly reduce the condition of the wood. Areas of incipient decay detected in wooden structures by the devices, systems, and methods of the disclosed technology may be treated with fumigants, or other materials, compositions, or treatments, to stop or slow down infection or invasion by, for example, wood decay fungi, thereby extending the useful life of the wooden structure. A characteristic of incipient decay may be that it may be arrested if the appropriate intervention or treatment may be applied while the incipient decay may be still in its early stages.

In an example embodiment, the device 100 may comprise a vertical handle 102, a distance sensor 104, a shaft 106, and an image capture device 108, as shown in FIG. 7. In some embodiments, the device may be a handheld device. In an example aspect, the device 100 may be used to automatically profile the condition, and as a result indicate the strength of a wooden structure 112. When introduced into a wooden structure 112, the image capture device 108 may be capable of capturing image data of the surrounding wood.

In some embodiments of the disclosed technology, the wooden structure 112 to be inspected may be comprised primarily of wood. In some example some embodiments, the wooden structure 112 may consist of a utility pole, a piling, a beam, a board, a timber, or any other type of wooden structure. The wooden structure 112 may consist of Western red cedar, Douglas-fir, southern pine, lodgepole pine, or any other species of wood.

In example embodiments, the shaft 106 of the probing device 100 may permit the image capture device 108 to be inserted into an inspection hole 160 in a wooden structure 112. The shaft 106 may be sufficiently long to allow inspection of underground portions of a wooden structure 112. When the shaft 106 is inserted into a wooden structure 112 at an angle toward the ground, as illustrated for example in FIG. 9, the shaft may probe portions of the structure underground, without the need to excavate the structure.

Preferably, the shaft 106 of the probing device may be substantially rigid. The rigidity of the shaft 106 may be optimized, for example, to help ensure accuracy and reliability of the measurements of a distance sensor 104 mounted to the shaft regarding the location of an image capture device 108 within a wooden structure 112.

The shaft 106 may be preferably electrically non-conductive, but not necessarily so. Examples of material suitable for use as a shaft 106 include, but are not limited to, metals, carbon fiber, polyester, fiberglass, polyester impregnated with fiberglass, and the like. However, the shaft 106 may be comprised of a number of different materials, including electrically non-conductive or conductive materials. Any material that is resistant to both compression and tension would be suitable. For example, thermal and non-thermally formed plastics (PLA, ABS), or wood. In other words, any material that is strong enough to push the tip through the inspection hole 160 may be suitable.

In some embodiments, the shaft 106 may be substantially cylindrical in shape, having a diameter slightly smaller than the diameter of the inspection hole, for example having a diameter that may be about 1% to about 10% less than the diameter of the inspection hole. In some embodiments, the shaft 106 may have a diameter of between the range of about 0.1875 to about 0.375 inches, more preferably between the range of about 0.200 to about 0.300 inches. In some embodiments, the diameter of the shaft 106 may be sufficiently large to support the image capture device 108, but small enough to be inserted into holes bored into a wooden structure 112 that are unlikely to harm the structural integrity of the wooden structure 112. Shafts having different diameters may be used to fit into various hole sizes (e.g., fume and inspection holes). In some embodiments, the shaft 106 may be non-cylindrical and capable of being inserted into bored inspection holes having an appropriate diameter, as described above. In some embodiments, the shaft 106 may be adjustable in length.

In embodiments of the disclosed technology, the length of the shaft 106 may be sufficient to enable inspection of a wooden structure 112, such as a utility pole. In some embodiments, the shaft 106 may be sufficiently long to permit inspection of the portion of a utility pole underground, including the shell (or surface) layers of the utility pole opposite the shell layers where the probing device is inserted into the utility pole. In some embodiments, the shaft 106 may be sufficiently long to enable inspection across the entire diameter of a utility pole at a 45-degree angle to the pole. As an example, the shaft may be about 24 to about 30 inches in length. In some embodiments, the length of the shaft may be adjustable. In some embodiments, the shaft 106 may be designed to fold for ease of transport. In some embodiments, the shaft 106 may be removable, or may comprise multiple removable sub-components. Embodiments of the device having a removable shaft may allow for different lengths or diameters of shafts to be used in the device.

The shaft 106 may comprise a probing tip 122 at the end of the shaft 106 nearest the image capture device 108, wherein the probing tip 122 surrounds one or more image capture devices 108 of the device. In some embodiments, the probing tip 122 has a diameter slightly smaller than the diameter of the inspection hole 160, but slightly larger than the base of the shaft 106. For example, the probing tip 122 may have a diameter that may be about 1% to 10% less than the diameter of the inspection hole, and about 1% to 10% greater than the diameter of the base of the shaft 106. In some embodiments, the diameter of the probing tip 122 may be between the range of about 0.1875 to about 0.375 inches, more preferably between the range of about 0.250 to about 0.375 inches. In some embodiments, the probing tip 122 may be a separate component from the shaft 106. In embodiments where the probing tip 122 collects debris in a bored hole, the probing tip 122 may have an additional slot for debris to exit. The probing tip 122 may be removable so that debris may be cleaned out or so that different attachments may be fastened to the tip of the shaft 106.

The shaft 106 may also comprise a tube 106a, as shown for example in FIG. 14. The tube 106a may be attached to the substantial remainder of the shaft using any attachment mechanism, including but not limited to a pin 119 or adhesive. The tube 106a portion of the shaft may be made of any material suitable to protect the components housed within the tube, including metal, carbon fiber, plastic, fiberglass, or other composite material. In some embodiments, the shaft 106 may be attached to a handle, for example a raised handle 101, vertical handle 102, horizontal handle 103, or dual-grip handle 115. The handle may be designed to facilitate careful and reliable insertion of a probing device 100 into a wooden structure. In some embodiments, the shaft 106 may include a safety cover to keep the image capture device 108 covered when the device is not in use. The shaft 106 may also be hollow in some embodiments.

Distance Sensor of the Device

In some embodiments, the distance sensor 104 may be any sensor that allows the determination and/or recording of the location or depth of the image capture device 108 in the wooden structure 112. The distance sensor 104 may include but is not limited to mechanical, electrical, optical and acoustical sensors, and the like. According to some embodiments, the distance sensor 104 may be a potentiometer. For example, a string potentiometer, using a retractable cable, may be used as a distance sensor 104 in the disclosed technology. As the cable moves, the potentiometer may output a range of voltage that may be correlated to location, distance, or depth. The string potentiometer may be attached to the device at the handle or at the shaft 106, or encased in a collapsing housing. An analog-to-digital converter may be electrically connected to the distance sensor 104 to convert an analog signal (e.g., variable voltage) to a digital output (e.g., distance). For example, a string potentiometer may run through an ADS1115 Analog-to-Digital Converter (from Texas Instruments). As another example, a trellis or scissors potentiometer may be used as a distance sensor 104. According to some embodiments, the distance sensor 104 may be a short-range sonar. For example, any short-range sonar may be used as a distance sensor 104 in the disclosed technology. An acoustic reflector may also be attached to the surface of the wooden structure.

In some embodiments of the disclosed technology, the distance sensor 104 may be mounted on the handle or the shaft 106 of the probing device 100. In some embodiments of the disclosed technology, the distance sensor 104 may consist of, for example, a short-range sonar, a laser, a short-range radar, or any other type of non-contact or contact distance sensor 104. In some embodiments, the distance sensor 104 may be a short-range sonar which may transmit a pulse of sound (also known as a "ping") from an acoustical transmit/receive array or an external transducer. The ping may reflect off the surface of the wooden structure 112 and may be received by the short-range sonar distance sensor 104. The distance sensor 104 may then use the speed of the transmitted ping and the elapsed time between the transmission and receipt of the ping to calculate the distance between the sensor 104 and the face of the wooden structure 112.

In some embodiments of the disclosed technology, as illustrated in FIG. 9, the distance sensor 104, for example a short-range sonar, may be oriented from about a 45-degree angle to about a 90-degree angle from the face of the wooden structure 112 while still receiving a sufficient return signal from the transmitted ping to provide the sensor 104 with an accurate distance reading. In this way, the probing device 100 may be inserted into a wooden structure 112 to inspect the portions of the structure underground, including the shell of the structure underground. In some embodiments, the angle may be adjustable between about 0 and about 45 degrees. According to some embodiments, the angle may be adjustable between about 0 and about 90 degrees. In some embodiments, the probing device may comprise an inclinometer. The inclinometer may be used, for example, to record the angle of the sonar to the shaft, record the angle of a bored hole to the ground, and/or to keep the sonar (or any other distance sensor) level.

In some embodiments of the disclosed technology, as illustrated in FIG. 18, the distance sensor 104 may comprise a potentiometer, for example, a string potentiometer, which measures the distance of the image capture device within a wooden structure. For example, a SP1 50 string potentiometer (from Celesco) may be used as a distance sensor 104 in the disclosed technology. In some embodiments, the probing device also may comprise an inclinometer. The inclinometer may be used, for example, to record the angle of the string potentiometer to the shaft 106, record the angle of a bored hole 160 to the ground-line 170, and/or to keep the string potentiometer level. In some embodiments, the inclinometer records the angle of the bored hole 160 to the ground-line 170, which, in conjunction with the distance or depth recorded by the potentiometer, may be used to determine the location of the image capture device 108 within the wooden structure 112. For example, the inclinometer may be an MMA7455 Digital Acceleration Title Angle Sensor Module (Freescale Semiconductor).

In some embodiments of the disclosed technology, the distance sensor 104 may comprise collapsible scissors 111 and a potentiometer. An example of this embodiment is illustrated in FIG. 20. The collapsible scissors 111 may be expanded along the length of the shaft 106 with a spring 117. The collapsible scissors 111 may collapse into the base of the shaft 106 when the probing tip 122 of this embodiment may be inserted into a wooden structure and the collapsible scissors 111 are pressed against the surface of the wooden structure. The magnitude that the collapsible scissors 111 collapse or fold back toward the base of the shaft 106 may be measured by a rotating potentiometer that produces variable voltage. The variable voltage may be then correlated to the distance or location of the image capture device 108 in the wooden structure, for example using an electronics unit and/or computing device attached to or remote from the device. An inclinometer may also be used in conjunction with the collapsible scissors 111 and the potentiometer to determine the location of the image capture device 108 within a wooden structure.

In some embodiments of the disclosed technology, the distance sensor 104 may comprise a potentiometer connected to a compression sleeve 113 around the shaft 106. An example of this embodiment is illustrated in FIG. 21. The compression sleeve 113 may include an elongated spring that expands along the length of the shaft 106 up to the image capture device 108. A potentiometer with a string or cable 104a may be attached to the end of the elongated spring closest to the image capture device 108, or elsewhere along the compression sleeve 113. When the image capture device 108 may be inserted into a hole 160 in a wooden structure 112, the compression sleeve 113 may press against the surface of the wooden structure 112 and compress back towards the base of the shaft 106. The magnitude that the compression sleeve 112 compresses may be measured by the string potentiometer, which may produce a variable voltage. The variable voltage may be then correlated to the distance or location of the image capture device 108 in the wooden structure, for example using an electronics unit and/or computing device attached to or remote from the device. An inclinometer may also be used in conjunction with the compression sleeve 113 and the string potentiometer to determine the location of the image capture device 108 within a wooden structure 112. A stop wire 121 may be secured to the dual-grip handle 115 and to the end of the compression sleeve 113 closest to the image capture device 108. The length of the stop wire 121 should be sufficient to prevent the compression sleeve 113 from extending beyond the end of the shaft 106. The stop wire 121 may comprise, for example a string, cable, or wire and may be metal or non-metal.

Image Capture Device

In example embodiments, the image capture device 108 of the probing device 100 may be designed to ride along the inside of a bore hole 160 within a wooden structure 112. When the shaft 106 of the probing device rides along an inspection hole 160, the image capture device 108 may be capable of capturing image data of the wood within the structure surrounding the image capture device 108, resulting in image data. In some embodiments of the disclosed technology, the image capture device 108 may be attached to the end of the shaft 106 opposite the handle. In some embodiments of the disclosed technology, the image capture device may be attached to the end of the shaft opposite the distance sensor 104. In some embodiments, the image capture device 108 may include a light source, or the probing device 100 itself may have an illumination source. According to some embodiments, image capture device 108 may include a retractable cover such that the image device 108 may be covered when it is first inserted into the inspection hole 160, but the cover may be then retracted as the probing device 100 is drawn out of the inspection hole 160, so that the image capture device 108 may capture image data.

In some embodiments, the image capture device 108 has a height substantially equal to the diameter of the shaft 106. In some embodiments, the image capture device 108 has a height substantially equal to the diameter of the probing tip 122. According to some embodiments, the image capture device 108 has a height in the range of about 0.1875 inches to about 0.375 inches. Further, in some embodiments, the image capture device has a length that may be greater than its height. However, an image capture device 108 may be of any size suitable for minimally invasive inspection of a wooden structure 112.

In some embodiments, the probing device 100 may comprise more than one image capture device 108. For example, in some embodiments, the probing device 100 may comprise a plurality of image capture devices 108. For example, a plurality of image capture devices or image sensors may be mounted in a 360-degree arrangement and may be configured to capture images of the wood surrounding the probing device 100. In some embodiments, probing device 100 may include an "orb" image capture device aligned with probing tip 122 (i.e., facing towards the end of the tip of the probing tip 122), which may be capable of capturing a wide area in a single instance of data capture. In this way, an immersive set of image data may be taken quickly. In some embodiments, a live "feed" of images may be available, allowing a user, wearing a virtual reality headset, to virtually "look" at the wood inside the inspection hole 160 in real time. According to some embodiments, multiple image capture devices (but fewer than would be used in a 360-degree arrangement) may be used to capture multiple angles at the same time to convey more image data at one time.

In some embodiments, the image capture device 108 may be a camera. According to some embodiments, the image capture device 108 may be a high-definition or higher camera. In some embodiments, the image capture device 108 may be capable of capturing image data in the electromagnetic spectrum outside of the range of human vision. In some embodiments, the image capture device 108 may be capable of capturing only still images. In some embodiments, the image capture device 108 may be capable of capturing only video. In some embodiments, the image capture device 108 may be capable of capturing both still images and video. According to some embodiments, the image capture device 108 may additionally be capable of capturing audio. In some embodiments, image capture device 108 may additionally provide a source of illumination, such as an LED light source or a laser light source.

According to some embodiments, the image capture device 108 may include one or more of an injection-molded body, an image sensor (e.g., CMOS, CCD, or CMOS pixel image sensor), a processor (e.g., for processing or transferring raw image data), and a processing unit for controlling the camera. In some cases, image capture device 108 may also include a mechanical lens and/or aperture with associated drive mechanisms to provide focusing or zooming ability. Various types and combinations of sensors, processors, lenses, and control mechanisms and circuitry may be utilized as well. In some embodiments, this image capture device 108 may be connected to the electronics unit 105. Further, in some embodiments, additional processing and storage of processed images are completed in the electronics unit 105. In some embodiments, raw or processed image data may be transmitted to an external processing system. According to some embodiments, raw or processed image data may be transmitted to an external storage or display system.

Methods and Systems for Evaluating a Wooden Structure

In some embodiments of the disclosed technology, an image capture device 108 may be inserted into a hole in a wooden structure 112 to gather data about the internal condition of that structure. The hole may be pre-drilled, or may be bored or drilled by the personnel conducting the inspection of the structure, by using a drill or a borer, for example. In some embodiments of the disclosed technology, the image capture device 108 may be inserted into a pre-drilled hole to avoid drilling new holes that may further compromise the integrity of the structure. In other some embodiments of the disclosed technology, the personnel conducting the inspection of the structure may choose to drill or bore a new hole in the structure to ensure that the wood surrounding the entrance of the hole is healthy, non-decayed wood that provides an accurate condition evaluation. In these some embodiments, the personnel may penetrate the exterior of the wooden structure with the drill or bore above the ground line of wooden structure, and then angle the drill or bore downwards so that at least a portion of the inspection hole in the interior of structure may be located below the ground-line of the structure, which may be a prime location for decay. In some embodiments of the disclosed technology, the inspection hole may be sufficiently small to permit the image capture device 108 to ride along the bore hole. For example, the diameter of the inspection hole may be essentially the same as, but not less than, the diameter of the shaft 106 of the probing device 100.

In one embodiment of the disclosed technology, a method of determining the condition of a wooden structure by operating a probing device 100 may comprise the steps of, as shown in FIG. 9, boring a hole into a wooden structure 112, inserting the probing device 100 into the bored hole, measuring the location of the image capture device 108 of the probing device 100 within the structure, capturing image data at the location using image capture device 108, and transmitting the location and image data to a computing device 116, and repeating this process multiple times (more than once) as the probe is removed from the bore hole, in order to obtain a complete visual profile of the interior surfaces of the wooden structure 112. In some embodiments, the image capture device 108 may capture video data as the probe 100 is inserted, or as it is removed, or both, in addition to or instead of capturing still-image data. In some embodiments, the location and image data measurements and transmissions are repeated at multiple locations within the wooden structure 112, and the data may be compiled and normalized by the computing device 116 to create a condition profile of the wooden structure 112. In some embodiments, the image data produced by the image capture device 108 may be then transmitted to a system 116, which may be then capable of recognizing various characteristics present in the image data, based on a model on which the system has been "trained." Based on this automated recognition of characteristics, the system 116 may be then capable of generating a report, or various graphical representations, of the condition of the wood at each depth measurement. In this way, the condition of the wooden structure 112 may be ascertained. In some embodiments, the wooden structure 112 may be subsequently subjected to remedial treatment, reinforcement, or replacement based on the condition of the wooden structure. In some embodiments, the wooden structure 112 may comprise a utility pole.

In some embodiments, the image capture device 108 may begin to capture image data immediately as it is moved further into the inspection hole. As the image capture device 108 proceeds through the inspection hole, the distance sensor 104 may measure the amount of insertion (i.e., depth) into the structure, and the image capture device 108 may collect image data from the surrounding wood. In some embodiments, each image data point may be measured and correlated to the distance the probe has traveled into the wooden structure 112, using, for example, a computing device 116 coupled to the distance sensor 104 and image capture device 108. The computing device 116 may be attached to the probing device 100, including for example a visual display to show results of an inspection, or be remote from the probing device 100.

In some embodiments, a computing device 116 capable of receiving and recording data from the distance sensor 104 and the image capture device 108, and may be coupled to the probing device 100. The computing device 116 may automatically record the location of the image capture device within the structure, indicated by the distance sensor 104, and the data captured by the image capture device 108 at that location.

In some embodiments, the computing device 116 may use the "trained" model to be able to recognize and categorize image data received from image capture device 108. In some embodiments, the training may be achieved by way of machine learning algorithms, where the system may be "trained" using a number of training images. According to some embodiments, machine learning may allow the system to learn various classifications relating to the condition of wood based on visual indicators, and to thus be able to categorize the conditions of various wooden structures. Various machine learning algorithms, known to those of skill in the art, may be used. In some embodiments, supervised machine learning algorithms may allow for rapid training of the system of computing device 116. In some embodiments, this "supervised" training involves training a system to correlate visual data with particular conditions or parameters, such as, as non-limiting examples, grain, color, hardness, moisture content, fiber strength, or fiber integrity. In some embodiments, this "supervised" training may be accomplished by utilizing training images, which already have grain characteristics indicated from a human operator ("labeled" images), and providing these images to the system. In this way, the system, through machine learning, may be able to recognize the desired condition parameter from unlabeled images. The system may then categorize the wood according to the model, to provide a conclusion as to the condition of the wood structure. Training images containing categorizations of various grain patterns, as well as colors, dirt, voids, other objects (such as insects and nails), and other forms of damage (such as partial voids and tears), are fed into the system, which may then "learn" what grain patterns, colors, and objects correspond to what type of categorizations. Once these categorizations are made, they may be communicated to the user. Additionally, based on rule sets (or, more machine learning based on training images or data), the system may draw conclusions concerning the condition of the wood. In some embodiments, the system may make recommendations as to what repair or replacement procedures, if any, should be undertaken, and at what locations.

According to some embodiments, the machine learning may take place using a semi-supervised algorithm, rather than a supervised algorithm. In some embodiments, the semi-supervised training consists of using fewer training images, and using a larger number of unlabeled images, in order to train the system of computing device 116. According to some embodiments, various methods of machine learning or other forms of training artificial intelligence systems may be used, and should not be restricted to the methods described herein.

According to some embodiments, the computing device 116 may be able to determine a profile of the interior surfaces of the wooden structure 112, by determining the locations of voids or any other type of decayed section from collected image data, and based on training images of approximate dimensions of spaces, may determine the length, height, and width of any decayed section within the wooden structure 112. In some embodiments, an operator 120 may repeat the steps of inserting the probing device 100 into a second inspection hole, and the computing device 116 again records the measurements. Image data from a single borehole may be normalized and integrated with data from additional boreholes in order to build a more complete image of any decayed sections within wooden structure 112, through processing performed in computing device 116. According to some embodiments, computing device 116 may be able to construct a three-dimensional visual representation of the interior surfaces of the wooden structure 112 around the area of the bored holes. In some embodiments, this generated visual representation may be displayed on an attached or remote display, for near real-time viewing by operators and other individuals.

In some embodiments, the probe 100 may be able to perform some repairs or maintenance activities automatically or at the direction of an operator. According to some embodiments, the probe tip 122 may have a heating mechanism or mechanism capable of creating an exposed electric arc, to neutralize insects in the probe tip's 122 path. In some embodiments, probe tip 122 may have an attached tube, which extends on its opposite end to outside the bored hole, and connects to a vacuum source, in order to remove small, loose debris in the path of probe tip 122.

In some embodiments, an operator 120 may insert a probing device 100 into an inspection hole 160, and carefully remove the probing device 100 back through the inspection hole 160 at a rotated angle from the initial entry, such that the probing device 100 observes the condition of another portion of wood within the structure along the inspection hole 160. As a non-limiting example, an operator 120 may insert the probing device 100 such that the image capture device 108 rides along the top of the inspection hole 160, and after penetrating through the inspection hole 160, the operator 120 may rotate the probing device 100 about 180 degrees, such that careful removal of the probing device 100 back through the wooden structure 112 results in the image capture device 108 riding along the bottom of the inspection hole 160.

In one embodiment of the disclosed technology, a system for evaluating the condition of a wooden structure 112 may comprise a probing device 100 coupled to a computing device 116, as shown in FIGS. 11A-11B. Examples of computing devices 116 that may be used in the disclosed technology include PC laptops or desktops, tablets, smartphones, and touch-screen devices. In some embodiments, the probing device 100 may collect image data via image capture device 108 within one or more locations within a wooden structure 112, and may transmit the image data and corresponding locations at which said data was collected to the computing device 116. The connection and transmission between the probing device 100 and the computing device 116 may be wireless, as shown in FIG. 11B. The computing device 116 may alternatively be attached to the probing device 100, so that an operator may view results at the same time as an inspection. The computing device 116 may then correlate the image data to location data to create a condition profile of the wooden structure 112.

In evaluating the condition of a wooden structure 112, the computing device 116 may be also capable of producing a condition profile, for example as illustrated in FIG. 12. In some embodiments, the condition profile demonstrates the chosen condition indicator of wood across an inspection hole of a utility pole. The example graph in FIG. 12 plots a measure of the chosen quality indicator, as a function of depth or location along an inspection hole within the utility pole. The vertical line at about the 16-inch value on the x-axis denotes the location where the image capture device 108 was introduced into the utility pole, and the vertical line at about the 6-inch value on the x-axis denotes the location where the image capture device 108 exited the opposite side of the utility pole. The results in FIG. 12 demonstrate a decreased condition indicator at the location where the probing device exited the wooden structure, which might indicate decay or decomposition in that portion of the wooden structure 112. In some embodiments, the computing device 116 may be attached to the probing device. In other embodiments, the computing device 116 may be remote from the probing device.

In some embodiments of the methods and systems of the disclosed technology, the wooden structure 112 may be subjected to remedial treatments, reinforcement, or replacement based on the condition of one or more areas of the structure. Examples of remedial treatments include preservative pastes (e.g., MP500-EXT) and bandages (e.g., Pole-Wrap™), fumigants (e.g., MITC-FUME®, Super-Fume, and Woodfume), solid rods (e.g., Bor8 Rods and copper-borate rods), and liquid treatments (e.g., Hollow Heart® CB). Preservative pastes and bandages may be applied, for instance, to address external decay in the areas of a wooden structure at or below ground-line. Fumigants may be applied, for instance, if the condition of the wooden structure indicates areas of internal early or incipient decay. Fumigants can produce vapors that diffuse and travel vertically and horizontally from applications, eliminating wood destroying fungi. Liquid treatments may be applied, for instance, if the condition of the wooden structure indicates areas of internal advanced decay, voids, or cavities. Solid rods may be installed, for example, in pre-drilled holes, such as bolt holes, pole tops, and cross arms, and generally comprise one or more water-soluble wood preservatives. In some embodiments, based on the condition of one or more areas of a wooden structure, reinforcement of a pole may be implemented by splinting or stubbing a pole using steel channel, reinforcing fiberglass, and epoxy, or by stubbing a pole using a steel channel or fiberglass reinforcing system.

Inspection and Maintenance of Wooden Structures

Condition profiles and information determined by the devices, systems, and methods may be used, for example, to determine the capacity remaining in a wooden structure or determine whether a wooden structure may be suitable for a particular load, identify structures for remedial treatment or reinforcement, regularly inspect and maintain in-place wooden structures, plan future inspection and maintenance actions of in-place wooden structures, identify a serviceable in-place wooden structure, identify a reinforceable reject in-place wooden structure, and/or identify a replacement candidate in-place wooden structure.

Regular inspection and maintenance of in-place wooden structures, such as wooden poles, may be essential to extending the useful life of these structures by ensuring that their wood retains its strength. A comprehensive maintenance program for wooden utility poles, for example, encompasses the monitoring of new attachments and loadings for poles to be some that the poles are sufficient to carry the new loadings, cyclical in-place inspection and restoration and replacement programs based on new loadings and the results of wood pole inspection, and emergency services. In-place wood pole inspection, as used herein, refers to a nondestructive or minimally-invasive inspection or nondestructive evaluation to determine strength loss in service of a highly variable material, wood, which has been processed, prior to installation, by treatment with wood preservatives to resist attack by wood-destroying organisms such as fungal decay and insects.

While the wood of wooden poles and other wooden structures are initially treated with preservatives that protect against both fungi and insects, loss of these preservatives over time from the wood may leave the structures susceptible to decay from the gradual deterioration caused by fungi and other low forms of plant life (e.g., algae) as well as from infestation by insects including termites, ants, and wood borers. Depending on their geographical location, wooden poles in the United States are classified as being located in one of five "Decay Severity Zones" by the U.S. Department of Agriculture's Rural Utilities Service. Zone 1, where the humidity and temperature are the least conducive to fungal growth and insect infestation, encompasses much of the mountainous West of the United States, whereas Zone 5, the most severe area of decay, is made up of the hot and humid coasts of the southeastern states.

A planned in-place inspection program for wooden poles serves several functions: identifying those poles which present a danger or risk of failure so that those poles may be removed and replaced, identifying poles which are in early stages of damage or decay so that remedial treatments or reinforcement may be applied to those still-serviceable poles to extend their serviceable life, and collecting data and information for planning future inspection and maintenance actions for a system of wood poles. Proper inspection and treatment of wooden poles, depending upon the decay hazards in the area, may extend the serviceable life of those poles by many years.

Spot checking may be the initial step in developing a planned pole inspection and maintenance program. Spot checking is a method of sampling representative groups of poles on a system to determine the extent of pole decay and to establish priority candidates for the pole maintenance measures of the program. A general recommendation is to inspect a 1,000-pole sample, made up of continuous pole line groupings of 50 to 100 poles in several areas of the system. The sample should be representative of the poles in place. For instance, all the poles on a line circuit or a map section should be inspected as a unit and not just the poles of some age group. Field data should be collected on the sample as to age, supplier, extent of decay, etc.

The data should be analyzed to determine the areas having the most severe decay conditions and to establish priorities for a pole-by-pole inspection of the entire system. It may be desirable to take additional samples on other portions or areas of the system to determine if the severity of decay is significantly different to warrant the establishment of an accelerated pole inspection and maintenance program for that portion of the system. The results of the spot check will aid in scheduling a continuous pole inspection and maintenance program at a rate commensurate with the incidence of decay.

The Rural Utilities Service suggests varying timing for a cyclical pole inspection schedule depending on the geographical Decay Zone in which the wooden poles are located, as the vulnerability of poles to decay is generally proportionate to the decay zone in which they are installed. Poles located in the low-decay Zone 1, for example, should be initially inspected within 12-15 years after installation, with subsequent re-inspection approximately 12 years, and with approximately 1 out of every 12 poles in the system being inspected as representatives of the entire system. In contrast, poles located in the high-decay Zones 4 and 5 should be initially examined within 8-10 years after installation, with subsequent re-inspection every 8 years, and with approximately 1 out of every 8 poles in the system being inspected as representatives of the entire system.

If a spot check indicates that decay is advanced in 1 percent of the pole sample, the inspection and maintenance program should be accelerated so that a higher percentage of poles are inspected and treated sooner than the suggested timelines discussed above. Conversely, if the decay rate is low for a particular decay zone or area in the system, the pole-by-pole inspection may be adjusted accordingly.

After an inspection of wooden poles has been completed, the inspection results are used to update pole plant records, evaluate pole conditions, plan future inspection and maintenance actions, and provide information for system map revisions. The inspection process will result in identifying the condition of each individual pole. The National Electric Safety Code (NESC) requires that if the strength of a structure deteriorates to the level of the overload capacity factors required at replacement, the structure must be replaced or rehabilitated. The inspection results should indicate if a pole is "serviceable" or a "reject."

The NESC designates that a pole is considered "serviceable" when a large portion of completely sound wood exists, or only early stages of decay are present that have not reduced the pole strength below NESC requirements. A pole that does not meet these conditions should be classified as a "reject." Examples of "reject" poles are those that have suffered decay, insect, mechanical, or woodpecker damage that has reduced the pole strength at the ground-line below NESC requirements, or those with hazardous above-ground conditions such as a split top.

Rejected poles may be classified further depending on the severity of their deterioration and whether they are reinforceable. A "reinforceable reject" is a rejected pole which is suitable for restoration of its ground-line bending capacity with an industry-accepted method of reinforcement. A "replacement" candidate is a rejected pole which is not suitable for necessary rehabilitation, and a "priority reject" is a rejected pole that has such severe decay/damage that it should be removed from service as quickly as possible.

Remedial treatments for serviceable wooden poles can interrupt the degradation of a structure by the addition of chemicals, such as pesticides, insecticides, and fungicides, which combat decay and extend the useful life of the structure. Remedial treatments include the application of external preservatives (e.g., pastes or bandages) used for ground-line treatment as well as internal treatments such as liquid internal preservatives, fumigants, and solids. Woodpecker damage may be repaired by plugging woodpecker holes with various materials and covering the plugged hole with a wire mesh to discourage further woodpecker attack. Reinforcement of a pole may be implemented by splinting or stubbing a pole using steel channel, reinforcing fiberglass, and epoxy.

All reference publications or patents cited herein are hereby incorporated by reference in their entirety.

What is claimed is:

1. A device for evaluating the condition of a wooden structure, the device comprising:
   a shaft;
   a distance sensor coupled to the shaft; and
   an image capture device coupled to the shaft, the distance sensor being configured to measure a location of the image capture device in the wooden structure; and
   a computing device configured to:
     receive image data from the image capture device; and
     create, based on the image data, a condition profile of the wooden structure, the condition profile showing an approximate length, height, and width of any decayed section in the wooden structure.

2. The device of claim 1, wherein the shaft comprises a first end and a second end, the distance sensor being coupled to the shaft nearer the first end than the second end, and the image capture device being coupled to the shaft nearer the second end than the first end.

3. The device of claim 1, wherein the shaft further comprises a probing tip that surrounds the image capture device.

4. The device of claim 1, further comprising:
   a retractable cover configured to:
     cover the image capture device when the shaft is inserted into the wooden structure, and
     uncover the image capture device when as the shaft is withdrawn from the wooden structure.

5. The device of claim 1, wherein the shaft comprises a probing tip configured to guide, align, or center the shaft within a hole bored in the wooden structure.

6. The device of claim 1, wherein the image capture device comprises a plurality of image capture sensors configured to capture images of an area surrounding at least a portion of the shaft.

7. The device of claim 1, further comprising at least one from among a laser light-source, a light-emitting diode (LED) light source, and an ultra-violet light source.

8. A method for evaluating the condition of a wooden structure, the method comprising:
   inserting at least a portion of a probing device into the wooden structure, the probing device comprising:
     a shaft;
     an image capture device coupled to the shaft;
     a distance sensor configured to measure a location of the image capture device in the wooden structure; and
     a computing device configured to:
       receive image data from the probing device; and
       create, based on the image data, a condition profile of the wooden structure, the condition profile showing an approximate length, height, and width of any decayed section in the wooden structure;
   determining, by the computing device and using data from the distance sensor, a location of the image capture device within the wooden structure;
   capturing image data from within the wooden structure using the image capture device at a first determined location within the wooden structure; and
   repeating determining and capturing at a second location of the wooden structure.

9. The method of claim 8, wherein the image data comprises images of interior surfaces of the wooden structure.

10. The method of claim 8, wherein an appearance of the wooden structure at one or more locations within the structure is correlated with the condition of the wood at a location within the structure.

11. The method of claim 8, wherein the method comprises evaluating the condition of an outer surface of the structure.

12. The method of claim 8, wherein
   the shaft connects the image capture device to the distance sensor, and
   the method further comprises inserting the shaft into a hole of the wooden structure which extends below ground level to detect internal decay in a wooden structure below ground level without excavation.

13. The method of claim 8 further comprising:
   receiving a plurality of images that the image capture device acquires inside the wooden structure at a plurality of locations within the structure; and
   categorizing the condition of the wooden structure based on the plurality of images received from the image capture device.

14. A system for evaluating the condition of a wooden structure, comprising:
   a probing device for evaluating the condition of the wooden structure, the probing device comprising:
     a shaft;
     a distance sensor coupled to the shaft; and
     an image capture device coupled to the shaft, the distance sensor being configured to measure a location of the image capture device in the wooden structure; and
   a computing device coupled to the probing device configured to:
     receive image data from the probing device,
     process the received image data, and
     create, based on the image data received from the probing device, a condition profile of the wooden structure, the condition profile showing an approximate length, height, and width of any decayed section in the wooden structure.

15. The system of claim 14, wherein the image data is correlated with the condition of the wooden structure at a location within the structure.

16. The system of claim 14, wherein the computing device is further configured to calculate a strength of the wooded structure based on the condition profile.

17. The device of claim 1, wherein
the shaft has an end and at least one outer wall, and
the image capture device is positioned such that an image capture sensor of the image capture device is facing outward from the at least one outer wall of the shaft.

* * * * *